US011033582B1

(12) United States Patent
Brewer, Jr. et al.

(10) Patent No.: US 11,033,582 B1
(45) Date of Patent: *Jun. 15, 2021

(54) METHODS FOR PRESERVING AND ADMINISTERING PRE-BETA HIGH DENSITY LIPOPROTEIN HAVING A PREDETERMINED MINIMUM LEVEL OF DEGRADATION

(71) Applicant: HDL Therapeutics, Inc., Vero Beach, FL (US)

(72) Inventors: Hollis Bryan Brewer, Jr., Potomac, MD (US); Michael M. Matin, Short Hills, NJ (US)

(73) Assignee: HDL Therapeutics, Inc., Vero Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/021,883

(22) Filed: Sep. 15, 2020

Related U.S. Application Data

(63) Continuation of application No. 16/225,210, filed on Dec. 19, 2018, now Pat. No. 10,821,133.

(60) Provisional application No. 62/611,098, filed on Dec. 28, 2017.

(51) Int. Cl.
*A61K 35/16* (2015.01)
*A61K 38/17* (2006.01)

(52) U.S. Cl.
CPC .............. *A61K 35/16* (2013.01); *A61K 38/17* (2013.01)

(58) Field of Classification Search
CPC .... A61K 35/16; A61K 38/17; A61K 38/1709; A61K 31/575; A61K 49/0004; A61K 9/0019; A61K 9/1275; A61B 5/4088; A61B 5/00; A61B 5/055; A61B 6/037; A61B 6/504; A61P 25/28; A61M 1/3486; A61M 1/3496; A61M 1/36; C07K 14/775
See application file for complete search history.

(56) References Cited

U.S. PATENT DOCUMENTS

| | | |
|---|---|---|
| 3,639,725 A | 2/1972 | Maniscalco |
| 3,647,624 A | 3/1972 | Evenson |
| 3,744,474 A | 7/1973 | Shaw |
| 3,958,939 A | 5/1976 | Jones |
| 3,983,008 A | 9/1976 | Shinozaki |
| 3,989,466 A | 11/1976 | Pan |
| 4,025,423 A | 5/1977 | Stonner |
| 4,066,011 A | 1/1978 | Ballentine |
| 4,086,218 A | 4/1978 | Shanbrom |
| 4,103,685 A | 8/1978 | Lupien |
| 4,124,509 A | 11/1978 | Iijima |
| 4,173,215 A | 11/1979 | Bureau |
| 4,234,317 A | 11/1980 | Lucas |
| 4,235,602 A | 11/1980 | Meyer |
| 4,258,010 A | 3/1981 | Rozsa |
| 4,311,586 A | 1/1982 | Baldwin |
| 4,350,156 A | 9/1982 | Malchesky |
| 4,391,711 A | 7/1983 | Jackson |
| 4,399,217 A | 8/1983 | Holmquist |
| 4,402,940 A | 9/1983 | Nose |
| 4,430,557 A | 2/1984 | Eichelberger |
| 4,435,289 A | 3/1984 | Breslau |
| 4,463,988 A | 8/1984 | Bouck |
| 4,481,189 A | 11/1984 | Prince |
| 4,522,809 A | 6/1985 | Adamowicz |
| 4,540,401 A | 9/1985 | Marten |
| 4,540,573 A | 9/1985 | Neurath |
| 4,591,505 A | 5/1986 | Prince |
| 4,613,501 A | 9/1986 | Horowitz |
| 4,615,886 A | 10/1986 | Purcell |
| 4,643,718 A | 2/1987 | Marten |
| 4,645,512 A | 2/1987 | Johns |
| 4,647,280 A | 3/1987 | Maaskant |
| 4,648,974 A | 3/1987 | Rosskopf |
| 4,668,398 A | 5/1987 | Silvis |
| 4,671,909 A | 6/1987 | Torobin |
| 4,676,905 A | 6/1987 | Nagao |
| 4,677,057 A | 6/1987 | Curtiss |
| 4,680,320 A | 7/1987 | Uku |
| 4,696,670 A | 9/1987 | Ohnishi |

(Continued)

FOREIGN PATENT DOCUMENTS

| | | |
|---|---|---|
| CA | 1271708 | 7/1990 |
| CH | 617582 | 6/1980 |

(Continued)

OTHER PUBLICATIONS

Waksman et al. A First-in-Man, Randomized, Placebo-Controlled Study to Evaluate the Safety and Feasibility of Autologous Delipidated High-Density Lipoprotein Plasma Infusions in Patients With Acute Coronary Syndrome. J American College of Cardiology, 2010. vol. 55, No. 24, pp. 2727-2735. (Year: 2010).*
Brown et al. Therapies to Increase ApoA-I and HDL-Cholesterol Levels. Drug Target Insights, 2008, vol. 3, pp. 45-54. (Year: 2008).*
Sacks et al. Selective delipidation of plasma HDL enhances reverse cholesterol transport in vivo. Journal of Lipid Research. vol. 50, pp. 894-907. (Year: 2009).*
Miida et al. Analytical performance of a sandwich enzyme immunoassay for pre1-HDL in stabilized plasma. J Lipid Research, vol. 44, 2003, pp. 645-650. (Year: 2003).*
Office Action dated Dec. 23, 2019 for U.S. Appl. No. 16/225,210.
Notice of Allowance dated Jul. 2, 2020 for U.S. Appl. No. 16/225,210 (pp. 1-8).

(Continued)

*Primary Examiner* — Marcela M Cordero Garcia
(74) *Attorney, Agent, or Firm* — Novel IP

(57) ABSTRACT

Systems and methods for acquiring, preserving, and administering delipidated plasma. Extracted delipidated plasma, comprising pre-beta HDL, is obtained and are spot tested to establish baseline amounts or concentrations of pre-beta HDL. The batches are subjected to preservation, stored, and then prepared again for use at some later date. A portion of the batch may be tested again to determine if the pre-beta HDL in the delipidated plasma has degraded or is no longer effective.

14 Claims, 6 Drawing Sheets

(56) References Cited

U.S. PATENT DOCUMENTS

| | | |
|---|---|---|
| 4,700,685 A | 10/1987 | Miller |
| 4,701,334 A | 10/1987 | Durth |
| 4,775,483 A | 10/1988 | Mookerjea |
| 4,832,034 A | 5/1989 | Pizziconi |
| 4,835,368 A | 5/1989 | Fortmann |
| 4,836,928 A | 6/1989 | Aoyagi |
| 4,879,037 A | 11/1989 | Utzinger |
| 4,895,558 A | 1/1990 | Cham |
| 4,908,354 A | 3/1990 | Seidel |
| 4,909,940 A | 3/1990 | Horowitz |
| 4,909,942 A | 3/1990 | Sato |
| 4,920,948 A | 5/1990 | Koether |
| 4,923,439 A | 5/1990 | Seidel |
| 4,935,204 A | 6/1990 | Seidel |
| 4,966,709 A | 10/1990 | Nose |
| 4,970,144 A | 11/1990 | Fareed |
| 5,026,479 A | 6/1991 | Bikson |
| 5,055,396 A | 10/1991 | Curtiss |
| 5,080,796 A | 1/1992 | Nose |
| 5,089,602 A | 2/1992 | Isliker |
| 5,112,956 A | 5/1992 | Tang |
| 5,116,307 A | 5/1992 | Collins |
| 5,126,240 A | 6/1992 | Curtiss |
| 5,128,318 A | 7/1992 | Levine |
| 5,152,743 A | 10/1992 | Gorsuch |
| 5,187,010 A | 2/1993 | Parham |
| 5,203,778 A | 4/1993 | Boehringer |
| 5,209,941 A | 5/1993 | Wuest |
| 5,211,850 A | 5/1993 | Shettigar |
| 5,236,644 A | 8/1993 | Parham |
| 5,256,767 A | 10/1993 | Salk |
| 5,258,149 A | 11/1993 | Parham |
| 5,279,540 A | 1/1994 | Davidson |
| 5,301,694 A | 4/1994 | Raymond |
| 5,354,262 A | 10/1994 | Boehringer |
| 5,391,143 A | 2/1995 | Kensey |
| 5,393,429 A | 2/1995 | Nakayama |
| 5,401,415 A | 3/1995 | Rauh |
| 5,401,466 A | 3/1995 | Foltz |
| 5,418,061 A | 5/1995 | Parham |
| 5,419,759 A | 5/1995 | Naficy |
| 5,424,068 A | 6/1995 | Filip |
| 5,476,715 A | 12/1995 | Otto |
| 5,484,396 A | 1/1996 | Naficy |
| 5,496,637 A | 3/1996 | Parham |
| 5,523,096 A | 6/1996 | Okarma |
| 5,529,933 A | 6/1996 | Young |
| 5,634,893 A | 6/1997 | Rishton |
| 5,637,224 A | 6/1997 | Sirkar |
| 5,652,339 A | 7/1997 | Lerch |
| 5,679,260 A | 10/1997 | Boos |
| 5,698,432 A | 12/1997 | Oxford |
| 5,707,673 A | 1/1998 | Prevost |
| 5,719,194 A | 2/1998 | Mann |
| 5,744,038 A | 4/1998 | Cham |
| 5,744,039 A | 4/1998 | Itoh |
| 5,753,227 A | 5/1998 | Strahilevitz |
| 5,853,725 A | 12/1998 | Salk |
| 5,855,782 A | 1/1999 | Falkenhagen |
| 5,858,238 A | 1/1999 | McRea |
| 5,877,005 A | 3/1999 | Castor |
| 5,885,578 A | 3/1999 | Salk |
| 5,895,650 A | 4/1999 | Salk |
| 5,911,698 A | 6/1999 | Cham |
| 5,916,806 A | 6/1999 | Salk |
| 5,919,369 A | 7/1999 | Ash |
| 5,928,930 A | 7/1999 | Salk |
| 5,948,441 A | 9/1999 | Lenk |
| 5,962,322 A | 10/1999 | Kozarsky |
| 5,980,478 A | 11/1999 | Gorsuch |
| 6,004,925 A | 12/1999 | Dasseux |
| 6,017,543 A | 1/2000 | Salk |
| 6,022,333 A | 2/2000 | Kensey |
| 6,037,323 A | 3/2000 | Dasseux |
| 6,037,458 A | 3/2000 | Hirai |
| 6,039,946 A | 3/2000 | Strahilevitz |
| 6,046,166 A | 4/2000 | Dasseux |
| 6,080,778 A | 6/2000 | Yankner |
| 6,127,370 A | 10/2000 | Smith |
| 6,136,321 A | 10/2000 | Barrett |
| 6,139,746 A | 10/2000 | Kopf |
| 6,156,727 A | 12/2000 | Garber |
| 6,171,373 B1 | 1/2001 | Park |
| 6,193,891 B1 | 2/2001 | Kent |
| 6,264,623 B1 | 7/2001 | Strahilevitz |
| 6,309,550 B1 | 10/2001 | Iversen |
| 6,337,368 B1 | 1/2002 | Kobayashi |
| 6,342,262 B1 | 1/2002 | Wuest |
| RE37,584 E | 3/2002 | Cham |
| 6,440,387 B1 | 8/2002 | Yankner |
| 6,472,421 B1 | 10/2002 | Wolozin |
| 6,605,588 B1 | 8/2003 | Lees |
| 6,706,008 B2 | 3/2004 | Vishnoi |
| RE39,498 E | 2/2007 | Cham |
| 7,361,739 B2 | 4/2008 | Bellotti |
| 7,375,191 B2 | 5/2008 | Bellotti |
| 7,393,826 B2 | 7/2008 | Bellotti |
| 8,030,281 B2 | 10/2011 | Bellotti |
| 8,048,015 B2 | 11/2011 | Bellotti |
| 8,268,787 B2 | 9/2012 | Bellotti |
| 8,637,460 B2 | 1/2014 | Bellotti |
| 2001/0028895 A1 | 10/2001 | Bisgaier |
| 2002/0055529 A1 | 5/2002 | Bisgaier |
| 2002/0081263 A1 | 6/2002 | Yankner |
| 2002/0107173 A1 | 8/2002 | Friedhoff |
| 2002/0128581 A1 | 9/2002 | Vishnoi |
| 2002/0183379 A1 | 12/2002 | Yankner |
| 2002/0188012 A1 | 12/2002 | Bisgaier |
| 2003/0018013 A1 | 1/2003 | Dasseux |
| 2003/0104350 A1 | 6/2003 | Bomberger |
| 2003/0127390 A1 | 7/2003 | Davis |
| 2003/0150809 A1 | 8/2003 | Bomberger |
| 2004/0106556 A1 | 6/2004 | Zhu |
| 2004/0170649 A1 | 9/2004 | Cham |
| 2005/0004004 A1* | 1/2005 | Bellotti ............. A61P 9/12 |
| | | 530/359 |
| 2005/0082271 A1 | 4/2005 | Kuhne |
| 2005/0158041 A1 | 7/2005 | Hoehne |
| 2005/0272162 A1 | 12/2005 | Fogelman |
| 2006/0060181 A1 | 3/2006 | Sasaki |
| 2006/0172939 A1* | 8/2006 | Bellotti ............ B01D 15/426 |
| | | 424/529 |
| 2006/0207440 A1 | 9/2006 | Matsuo |
| 2007/0272675 A1 | 11/2007 | Kuhne |
| 2008/0214438 A1 | 9/2008 | Bellotti |
| 2008/0227726 A1 | 9/2008 | Bellotti |
| 2008/0230465 A1 | 9/2008 | Bellotti |
| 2008/0234621 A1 | 9/2008 | Bellotti |
| 2011/0318423 A1 | 12/2011 | Bellotti |
| 2013/0052167 A1 | 2/2013 | Bellotti |
| 2014/0107029 A1 | 4/2014 | Bellotti |
| 2016/0324925 A1 | 11/2016 | Bellotti |
| 2017/0174747 A1 | 6/2017 | Bellotti |
| 2017/0319643 A1 | 11/2017 | Remaley |
| 2018/0355021 A1 | 12/2018 | Bellotti |
| 2019/0070257 A1* | 3/2019 | Brewer, Jr. .......... C07K 14/775 |
| 2019/0351112 A1* | 11/2019 | Brewer, Jr. .......... B01D 15/10 |
| 2019/0381070 A1* | 12/2019 | Brewer, Jr. .......... A61B 6/504 |
| 2020/0171086 A1* | 6/2020 | Brewer, Jr. .......... A61K 35/16 |

FOREIGN PATENT DOCUMENTS

| | | |
|---|---|---|
| CN | 1189378 | 8/1998 |
| DE | 2944138 | 6/1981 |
| DE | 3118072 | 11/1982 |
| DE | 3213390 | 10/1983 |
| DE | 3310263 | 9/1984 |
| DE | 19626955 | 1/1998 |
| EP | 36283 | 9/1981 |
| EP | 267471 | 5/1988 |
| EP | 436703 | 7/1991 |
| EP | 1016832 | 7/2000 |
| EP | 1641421 | 4/2006 |
| EP | 1669676 | 6/2006 |

(56) References Cited

FOREIGN PATENT DOCUMENTS

| | | |
|---|---|---|
| EP | 2368565 | 9/2011 |
| FR | 2571971 | 4/1986 |
| JP | 127104 | 10/1980 |
| JP | 277303 | 10/1993 |
| RU | 1116396 | 9/1984 |
| RU | 1204224 | 1/1986 |
| RU | 1752187 | 7/1992 |
| WO | 1988009345 | 12/1988 |
| WO | 1991001674 | 2/1991 |
| WO | 1995003840 | 2/1995 |
| WO | 1998009345 | 3/1998 |
| WO | 19732240 | 4/1999 |
| WO | 1999038498 | 8/1999 |
| WO | 2001045718 | 6/2001 |
| WO | 2001056579 | 8/2001 |
| WO | 2002000266 | 1/2002 |
| WO | 2002010768 | 2/2002 |
| WO | 2002030863 | 4/2002 |
| WO | 2002062824 | 8/2002 |
| WO | 2003000372 | 1/2003 |
| WO | 2003000373 | 1/2003 |
| WO | 2007144572 | 12/2007 |
| WO | 2019133358 A2 | 7/2019 |

OTHER PUBLICATIONS

Afana, M et al, "Hospitalization costs for acute myocardial infarction patients treated with percutaneous coronary intervention in the United States are substantially higher than Medicare payments", Clin Cardiol, 2015. 38(1): p. 13-9.

Shah, P.K., "Residual risk and high-density lipoprotein cholesterol levels: is there a relationship?" Rev Cardiovasc Med, 2011. 12(2): p. e55-9.

Nicholls, S.J. et al "Effect of two intensive statin regimens on progression of coronary disease", N Engl J Med, 2011. 365(22): p. 2078-87.

Brewer, H.B., Jr., "Clinical review: The evolving role of HDL in the treatment of high-risk patients with cardiovascular disease", J Clin Endocrinol Metab, 2011. 96(5): p. 1246-57.

Brown M S et al, "A receptor-mediated pathway for cholesterol homeostasis", Science, Apr. 4; 1986 232(4746):34-47. [PubMed: 3513311].

Hopkins P N et al, "Familial hypercholesterolemias: prevalence, genetics, diagnosis and screening recommendations from the National Lipid Association Expert Panel on Familial Hypercholesterolemia", J Clin Lipidol. Jun. 2011; 5(3 Suppl):S9-17. [PubMed: 21600530].

"Familial Hypercholesterolemia", https://rarediseases.org/rare-diseases/familial-hypercholesterolemia/ accessed Dec. 3, 2017.

Nordestgaard B G et al, "Familial hypercholesterolaemia is underdiagnosed and undertreated in the general population: guidance for clinicians to prevent coronary heart disease", Consensus Statement of the European Atherosclerosis Society. Eur Heart J. 2013; 34(45):3478-90a. [PubMed: 23956253].

Knowles et al, "Cascade Screening for Familial Hypercholesterolemia and the Use of Genetic Testing", JAMA Jul. 25, 2017; 318(4):381-382.

Bouhairie VE et al, "Familial Hypercholesterolemia", Cardiol. clin. May 2015:33(2): 169-179.

Cuchel M et al, "Homozygous Familial Hypercholesterolaemia: New Insights and Guidance for Clinicians to Improve Detection and Clinical Management", Eur Heart J. 2014; 35(32):2146-2157. [PubMed: 25053660].

Gagne C et al, "Efficacy and safety of ezetimibe coadministered with atorvastatin or simvastatin in patients with homozygous familial hypercholesterolemia", Circulation. May 28, 2002;105(21):2469-75.

Insull, "Clinical utility of bile acid sequestrants in the treatment of dyslipidemia: a scientific review", Southern Med J. 2006;99:257-73.

Rader DJ et al, "Lomitapide and mipomersen: two first-in-class drugs for reducing low-density lipoprotein cholesterol in patients with homozygous familial hypercholesterolemia", Circulation. Mar. 4, 2014;129(9):1022-32. doi: 10.1161/CIRCULATIONAHA.113.001292.

Cuchel M et al, "Efficacy and safety of a microsomal triglyceride transfer protein inhibitor in patients with homozygous familial hypercholesterolaemia: a single-arm, open-label, phase 3 study" Lancet. Jan. 5, 2013;381(9860):40-6. doi: 10.1016/S0140-6736(12)61731-0. Epub Nov. 2, 2012.

Thompson GR, "LDL apheresis", Atherosclerosis, Mar. 2003;167(1):1-13.

"PCSK9 Inhibitors: A New Option in Cholesterol Treatment", https://www.drugs.com/slideshow/pcsk9-inhibitors-a-new-option-in-cholesteroltreatment-1166, Accessed Dec. 16, 2017.

Rohatgi et al, "HDL cholesterol efflux capacity and incident cardiovascular events", N Engl J Med. Dec. 18, 2014;371(25):2383-93. doi: 10.1056/NEJMoa1409065. Epub Nov. 18, 2014.

Qiu C et al, "High-density lipoprotein cholesterol efflux capacity is inversely associated with cardiovascular risk: a systematic review and meta-analysis", Lipids Health Dis. Nov. 10, 2017;16(1):212. doi: 10.1186/s12944-017-0604-5.

El Kenz H et al, "Transfusion-related acute lung injury", Eur J Anaesthesiol. Jul. 2014;31(7):345-50. doi: 10.1097/EJA.0000000000000015.

British Committee for Standards in Haematology, "Guidelines for the use of fresh-frozen plasma, cryoprecipitate and cryosupernatant", Br J Haematol. 2004;126:11-28. [PubMed].

Carlebjork G, Blomback M, Pihlstedt P., "Freezing of plasma and recovery of factor VIII", Transfusion. Mar.-Apr. 1986;26(2):159-62.

"Plasma & Cryo", http://bca.coop/products-services/blood-products/plasma/ Accessed Nov. 17, 2017.

"Review of Standards for Plasma Products for Transfusion", Issue Summary, Blood Products Advisory Committee Meeting, Mar. 17, 2005, Gaithersburg, MD.

http://www.heart.org/HEARTORG/Conditions/Cholesterol/CausesofHighCholesterol/Familial-Hypercholesterolemia-FH_UCM_493541_Article.jsp#.WgnOvrbMwWo accessed Nov. 13, 2017.

International Search Report for PCT/US18/66389, dated Apr. 22, 2019.

Nakabayashi, et al.: "Degradation of pre-beta-high density lipoproteins and their binding activity to human blood monocytes". Ann Clin Lab Sci. Summer 2004, vol. 34, No. 3, pp. 287-298. Especially abstract, p. 288 col. 2 para 2, p. 289 col. 1 para 3, p. 291 col. 1 para 1, p. 291 fig 2C, 2D, p. 293 fig 5, p. 295 col. 2 para 2, p. 296 col. 2 para 2.

Barrans et al., "Pre-Beta HDL: Structure and Metabolism", Biochimica et Biophysica Acta, vol. 1300, No. 2, Apr. 19, 1996, pp. 73-85.

Akerblom, O, Bremme, K., Dackland, A.-L., Fatah, K., Suontaka, A.-M., and Blomback, M. (1992): "Freezing technique and quality of fresh frozen plasma'", Infusiontherapie, 19, 283-287.

Allain, J.P., Friedli, J., Morgenthaler, J., Pflugshaupt, R., Gunson, H.H., Lane, R.S., Rock, G.A., Schorr, J.B., Menache-Aronson, D., Stryker, M.H., Woods, K.R., (1983): "What Are the Critical Factors in the Production and Quality Control of Frozen Plasma Intended for Direct Transfusion or for Fractionation to Provide Medically Needed Labile Coagulation Factors?" Vox Sang 44, 246-259.

Farrugia, A. and Prowse, C. (1985): "Studies on the procurement of blood coagulation factor VIII: effects of plasma freezing rate and storage conditions on cryoprecipitate quality", J Clin Pathol 38, 433-437.

Favaloro, E.J., Soltani S., McDonald, J., (2004): "Potential laboratory misdiagnosis of hemophilia and von Willebrand disorder owing to cold activation of blood samples for testing", Am J Clin Pathol, 122, 686-692.

Hogman, C.F., Knutson, F., Loof, H.,(1998): "Storage of whole blood before separation: the effect of temperature on red cell 2, 3 DPG and the accumulation of lactate", Transfusion, 39, 492-497.

Koerner, K. and Stampe, D. (1982): "Stability of factors of the coagulation system in fresh frozen plasma during storage at −40 ° C and −20 ° C", Blut 45, 76, Abstract Only.

Kotitschke, R., Morfeld, F., Kirchmaier, C.-M., Koerner, K., and Kohler, M. (2000); "Stability of Fresh Frozen Plasma: Results of 36-Month Storage at −20 ° C, −25 ° C, −30 ° C and −40 ° C", Infus Ther Transfus Med 27, 174-180.

(56) References Cited

OTHER PUBLICATIONS

Over, J., and Loos, J.A. (1990): "Preservation and storage of human blood plasma proteins", in Smit Sibinga, C.Th., Das, P.C., and Meryman, H.T. ed., Cryopreservation and Low Temperature Biology in Blood Transfusion, in Developments in Hematology and Immunology 24, Dordrecht, 203-213.

Pietersz, R.N.I., de Korte, D., Reesink, H.W., Dekker, W.J.A., van den Ende, A., and Loos, J.A. (1989): "Storage of whole blood for up to 24 hours at ambient temperature prior to component preparation", Vox Sang 56, 145-150.

Woodhams, B., Girardot, O., Blanco, M.-J., Colesse, G., and Gourmelin, Y. (2001): "Stability of coagulation proteins in frozen plasma", Blood Coagulation and Fibrinolysis 12, 229-236.

U.S. Appl. No. 12/042,924 , "Final Office Action".

U.S. Appl. No. 13/222,287 , "Notice of Allowance", dated May 16, 2012, 36 pages.

U.S. Appl. No. 13/222,287 , "Office Action", dated Feb. 13, 2012, 7 pages.

U.S. Appl. No. 13/222,287 , Office Action Response, dated Apr. 24, 2012, 6 pages.

U.S. Appl. No. 13/601,131 , "Final Office Action", dated Jun. 5, 2013, 11 pages.

U.S. Appl. No. 13/601,131 , "Non-Final Office Action".

U.S. Appl. No. 13/601,131 , "Notice of Allowance", dated Jul. 3, 2013, 10 pages.

U.S. Appl. No. 13/601,131 , "Notice of Allowance", dated Sep. 16, 2013, 8 pages.

U.S. Appl. No. 14/133,997 , "Non-Final Office Action", dated Jan. 21, 2016, 8 pages.

U.S. Appl. No. 15/214,683 , "Non-Final Office Action", dated Sep. 9, 2016, 8 pages.

Agnese et al., "Evaluation of Four Reagents for Dilipidation of Serum", Clin Biochem, vol. 18, No. 2, 1983, pp. 98-100.

Albouz et al., "Extraction of Plasma Lipids Preserving Antigenic Properties of Proteins and Allowing Quantiation of Gangliosides by Neuraminic Acid Determination", Annales de Biologie Clinique, vol. 37(5), 1979, pp. 287-290.

Andre et al., "Characterization of Low- and Very-Low-Density Hepatitis C Virus RNA-Containing Particles", Journal of Virology, vol. 76, No. 14, Jul. 2002, pp. 6919-6928.

Asztalos et al., "Distribution of Apo A-I-Containing HDL Subpopulations in Patients with Coronary Heart Disease", Arteriosclerosis, Thrombosis, and Vascular Biology, vol. 20, Dec. 2000, pp. 2670-2676.

Asztalos et al., "Presence and Formation of Free Apolipoprotein A-I-Like Particles in Human Plasma", Arteriosclerosis, Thrombosis, and Vascular Biology, vol. 15, Sep. 1995, pp. 1419-1423.

Asztalos et al., "Role of Free Apolipoprotein A-I in Cholesterol Efflux", Arteriosclerosis, Thrombosis, and Vascular Biology, vol. 17, Sep. 1997, pp. 1630-1636.

Badimon et al., "High Density Lipoprotein Plasma Fractions Inhibit Aortic Fatty Streaks in Cholesterol-Fed Rabbits", Laboratory Investigation, 1989, 60, 455-461.

Badimon et al., "Regression of Atherosclerotic Lesions by High Density Lipoprotein Plasma Fraction in the Cholesterol-Fed Rabbit", J. Clinical Investigation, 1990, 85, 1234-1241.

Barrans et al., "Hepatic Lipase Induces the formation of pre-beta 1 high densitiy lipoprotein (HDL) from tricylglycerol-righ HDL2. A Study comparing liver perfusion to in vitro Incubation with lipases", Journal of Biological Chemistry, vol. 269, No. 15, Apr. 15, 1994, pp. 11572-11577.

Barrans et al., "Hepatic Lipase Induces the Formation of Pre-beta 1 High Density Lipoprotein (HDL) from Triacylglycerol Arich HDL2, A study comparing liver perfusion to in vitro incubation with lipases", Journal of Biological Chemistry, vol. 269, No. 15, Apr. 15, 1994, pp. 11578-11583.

Barres et al., "Cholesterol—Making or Breaking the Synapse", Science, vol. 294, No. 5545, Nov. 9, 2001, pp. 1296-1297.

Blanche et al., "Characterization of Complexes of Egg Yolk Phosphatidylcholine and Apolipoprotein A-II Prepared in Absence and Presence of Sodium Cholate", Biochimica et Biophysica Acta, 1988, v. 958, pp. 143-152.

Bloom et al., "Quantitation of Lipid Profiles from Isolated Serum Lipoproteins using Small Volumes of Human Serum", Clin. Biochem, vol. 14 (Abstract only), Jun. 1981, pp. 119-125.

Burns et al., "Use of In Vivo Models to Study the Role of Cholesterol in the Etiology of Alzheimer's Disease", Neurochem Res. Jul. 2003;28(7):979-86., Jul. 2003, 979-86.

Calero et al., "Functional and Structural properties of lipid-associated apolipoprotein J (clusterin)", Biochemical Journal, vol. 344, Issue 2, Dec. 1, 1999, pp. 375-383.

Cham et al., "Changes in Electrophoretic Mobilities of alpha- and beta-Lipoproteins as a Result of Plasma Delipidation", Clinical Chemistry, 1976, v. 22, 305-309.

Cham et al., "Heterogeneity of Lipoprotein Beta", Biochemical and Biophysical Research Communications, 1981, v. 103, 196-206.

Cham et al., "Importance of Apolipoproteins in Lipid Metabolism", Chem. Biol. Interactions, vol. 20, 1978, pp. 263-277.

Cham et al., "In Vitro Partial Relipidation of Apolipoproteins in Plasma", J. Biol. Chem, 1976, v. 251, 6367-6371 (Abstract only).

Cham et al., "Lipid Apheresis in an Animal Model Causes Acute Reduction in Plasma Lipid Concentrations and Mobilisation of Lipid from Liver and Aorta", Pharmacol (Life Sci. Adv.), 1994, v. 13, 25-32.

Cham et al., "Lipid Apheresis in an Animal Model Causes In Vivo Changes in Lipoprotein Electrophoretic Patterns", J. Clin. Apheresis, 1996, v. 11, 61-70.

Cham , "Nature of the Interaction Between Low-Density Lipoproteins and Polyanions and Metal Ions, as Exemplified by Heparin and Ca2", Clinical Chemistry, 1976, v. 22, pp. 1812-1816.

Cham et al., "Phospholipids in EDTA—Treated Plasma and Serum", Clinical Chemistry, 1993, 39, 2347-2348.

Cham et al., "Rapid Regression of Atherosclerosis by Cholesterol Alpheresis—Newly Developed Technique", 59th Congress European Atherosclerosis Society, Nice, France, May 17-21, 1992 (Abstract only).

Cham et al., "Rapid, Sensitive Method for the Separation of Free Cholesterol from Ester Cholesterol", Clinica Chimica Acta, 1973, v. 49, 109-113.

Cham et al., "A solvent system for delipidation of plasma or serum without protein precipitation", Journal of Lipid Research, 1976, vol. 17, pp. 176-181.

Cham et al., "Lipid Apheresis: An In Vivo Application of Plasma Delipidation with Organic Solvents Resulting in Acute Transient Reduction of Circulating Plasma Lipids in Animals", Journal of Clinical Apheresis, 1995, pp. 61-69.

Clay et al., "Formation of Apolipoprotein-Specific High-density Lipoprotein particles from Lipid-Free Apolipoproteins A-1 and A-11", Biochem. J., Feb. 1, 1999, 337, 445-451.

Collet et al., "Differential Effects of Lecithin and Cholesterol on the Immunoreactivity and Confirmation of Apolipoprotein A-I in High Density Lipoproteins", Journal of Biological Chemistry, May 15, 1991, v. 266(14), 9145-9152.

Cooper , "Dietary Lipids in the Aetiology of Alzheimer's Disease: Implications for Therapy", Drugs Aging, 2003, v. 20(6), 399-418 (Abstract only).

Cruzado et al., "Characterization and Quantitation of the Apoproteins of High-Density Lipoprotein by Capillary Electrophoresis", Analytical Biochemistry, vol. 243(1), Dec. 1996, pp. 100-109.

Dass et al., "Apolipoprotein A-1, Phospholipid Vesicles, and Cyclodextrins as Potential Anti-Atherosclerotic Drugs: Delivery, Pharmacokinetics, and Efficacy", Drug Delivery, vol. 7, 2000, pp. 161-182.

Deva et al., "Establishment of an in-use testing method for evaluating disinfection of surgical instruments using the duck hepatitis B model", J. Hosp. Infect. vol. 22, No. 2, 1996, 119-30.

Durbin et al., "The Effect of Apolipoprotein A-II on the Structure and Function of Apolipoprotein A-I in a Homogeneous Reconstituted High Density Lipoprotein Particle", The Journal of Biological Chemistry v. 272(50), pp. 31333-31339.

(56) References Cited

OTHER PUBLICATIONS

Durbin et al., "Lipid-free Apolipoproteins A-I and A-II promote remodeling of reconstituted high density lipoproteins and alter their reactivity with lecithin: cholesterol acyltransferase", Journal of Lipid Research, vol. 40, No. 12, 1999, pp. 2293-302.
Dwivedy, "Increase of Reverse Cholesterol Transport by Cholesterol Apheresis Regression of Atherosclerosis", 18th Australian Atherosclerosis Society Conference, Surfers Paradise, 1992, p. 21.
Eisenhauer et al., "Selective Removal of Low Density Lipoproteins (LDL) by Precipitation at Low pH: First Clinical Application of the HELP System", Klin Wochenschr (KWH), 1987, 65, 161-168.
European Application No. 04718501.2, "Office Action", dated Feb. 5, 2014, 7 pages.
European Application No. 04718501.2, "Response to Office Action in Related European Application No. 04 718 501.2", dated May 28, 2014, 8 pages.
European Application No. 10185381.0, "Extended European Search Report", dated Aug. 12, 2011, 8 pages.
European Application No. 10 185 381.0, "Response to Office Action", dated Aug. 7, 2013, 7 pages.
European Application No. 10185381.0, "Office Action", dated Sep. 10, 2014, 3 pages.
European Application No. 10185381.0, "Office Action", dated Feb. 7, 2014, 5 pages.
European Application No. 10185381.0, "Response to Office Action in Related European Application No. 10 185 381.0", dated May 28, 2014, 6 pages.
Fang et al., "In Vivo Rapid Mobilization of Adipose Tissue by Lipid Apheresis—A Newly Developed Technique", 18th Australian Atherosclerosis Society Conference, Gold Coast, Australia, 1992.
Feinstone et al., "Inactivation of Hepatitis B Virus and Non-A, Non-B Hepatitis by Chloroform", Infection and Immunity, vol. 41, No. 2, Aug. 1983, 816-21.
Gasparini et al., "Peripheral Markers in testing pathophysiological hypotheses and diagnosing Alzheimer's disease", Faseb. J., 1998, 12, 17-34.
Gauthier et al., "Alzheimer's Disease: Current Knowledge, Management and Research", Canadian Medical Association Journal, vol. 157(8), Oct. 1997, pp. 1047-1052.
Golde et al., "Cholesterol Modulation as an Emerging Strategy for the Treatment of Alzheimer's Disease", Drug Discovery Today, Oct. 15, 2001, 6(20), 1049-1055 (Abstract only).
Greicius et al., "Presenile Dementia Syndromes: An update on Taxonomy and diagnosis", J. Neurol. Neurosurg. Psychiatry, 2002, 72, 691-700.
Haas et al., "Apolipoprolein E forms stable complexes with recombinant Aizheimer's disease B-amyloid precursor protein", Biochemical Journal, Jan. 1, 1997, vol. 325, 169-175.
Hatch et al., "Practical Methods for Plasma Lipoprotein Analysis", Advances in Lipid Research, vol. 6, 1968, pp. 61-68.
Horowitz et al., "Viral Safety of Solvent/detergent-treated Blood Products", Blood Coagulation and Fibrinolysis, vol. 5, Suppl. 3, Dec. 1994, pp. S21-S28.
Innerarity et al., "Enhanced Binding by Cultured Human Fibroblasts of Apo-E Containing Lipoproteins as Compared with Low Density Lipoproteins", Biochemistry, vol. 17(8), Apr. 1978, pp. 1449-1447.
Ito et al., "Cholesterol-Sphingomyelin Interaction in Membrane and Apolipoprotein-mediated Cellular Cholesterol Efflux", J. of Lipid Research, Jun. 2000, vol. 41, pp. 894-904.
Jackson et al., "Isolation and Characterization of the Major Apolipoprotein from Chicken High Density Lipoproteins", Biochimica et Biophysica Acta, 1976, v. 420, 342-349.
Klimov et al., "Extraction of Lipids from Blood Plasma and Subsequent Introduction of Autologous Delipidized Plasma into the Body as a Possible Means to Treat Atherosclerosis", Russian Journal Kardiologia vol. 18, No. 6, 1978, 23-9.
Koizumi et al., "Behaviour of Human Apolipoprotein A-1: Phospho-Lipid and apoHDL: Phospholipid Complexes in Vitro and After Injection Into Rabbits", Journal of Lipid Research, vol. 29, 1988, pp. 1405-1415.

Kostner et al., "Beyond LDL-Cholesterol: New Treatments Raising HDL-Cholesterol or Enhancing Reverse Cholesterol Transport", Journal fur Kariologie, vol. 7-8, Sep. 2002, pp. 328-331.
Kostner et al., "Increase of APO AI Concentration in Hypercholesteraemic Chickens after Treatment with a Newly Developed Extracorpreal Lipid Elimination", 11th International Symposium on Drugs Affecting Lipid Metabolism, May 1992.
Kostner et al., "Lecithin-cholesterol acyltransferase activity in Normocholesterolaemic and Hypercholesterolaemic Roosters: Modulation by Lipid Apheresis", European Journal of Clinical Investigation, vol. 27(3), May 1997, pp. 212-218.
Koudinov et al., "Alzheimer's amyloid beta interaction with normal human plasma high density lipoprotein: association with apolipoprotein and lipids", Clin Chim Acta. 270(2), Feb. 23, 1998, 75-84.
Koudinov et al., "Alzheimer's soluble amyloid beta protein is secreted by HepG2 cells as an apolipoprotein", Cell Biol Int. May 1997; 21(5), May 1997, 265-71.
Koudinov et al., "Biochemical characterization of Alzheimer's soluble amyloid beta protein in human cerebrospinal fluid: association with high density lipoproteins", Biochem Biophys Res Commun. 223(3), Jun. 25, 1996, 592-7.
Koudinov et al., "Cholesterol's Role in Synapse Formation", Science. Mar. 22, 2002;295(5563), Mar. 22, 2002, 2213.
Koudinova et al., "Amyloid Beta, Neural Lipids, Cholesterol and Alzheimer's Disease", Neurobiology of Lipids, vol. 1, 2002, 27.
Kunitake et al., "Interconversion between Apolipoprotein A-1-containing Lipoproteins of Pre-beta and Alpha Electrophoretic Mobilities", J. Lipid Res., Dec. 1992, vol. 33(12), 1807-1816.
Ladu et al., "Association of Human, Rat, and Rabbit Apolipoprotein E with B-amyloid", Journal of Neuroscience Research, 1997, v. 49 (1),9-18.
Lipid Sciences, "Lipid Technology", http:llwww.lipidsciences.com/technology.html, Aug. 25, 2001, 1-4.
Lupien et al., "A New Approach to the Management of Familial Hypercholesterolaemia: Removal of Plasma-Cholesterol Based on the Principle of Affinity Chromatography", Lancet, vol. 1(7972), Jun. 1976, pp. 1261-1265.
Matz et al., "Reaction of Human Lecithin Cholesterol Acyltransferase with Synthetic Micellar Complexes of Apolipoprotein A-1, Phosphatidylcholine, and Cholesterol", The Journal of Biological Chemistry, vol. 257, Apr. 1982, pp. 4541-4546.
Mauch et al., "CNS Synaptogenesis Promoted by Glia-Derived Cholesterol", Science, Nov. 9, 2001, v. 294, 1354-1357.
Moya et al., "A Cell Culture System for Screening Human Serum for Ability to Promote Cellular Cholesterold Efflux", Arteriosclerosis and Thrombosis, vol. 14, issue 7, Jul. 1994, pp. 1056-1065.
Nakawatase et al., "Alzheimer's Disease and Related Dementias", Cecil's Text Book of Medicine, 2000, 21st Edition, 1, W.B. Saunders Company, 2042-2045.
Ngu, "Chronic Infections from the Perspective of Evolution: a Hypothesis", Medical Hypothesis, 1994, vol. 42, pp. 81-88.
Ngu, "Human Cancers and Viruses: A Hypothesis for Immune Destruction of Tumours Caused by Certain Enveloped Viruses Using Modified Viral Antigens", Medical Hypotheses, 1992, vol. 39, pp. 17-21.
Ngu, "The viral envelope in the evolution of HIV: a hypothetical approach to inducing an effective immune response to the virus", Medical Hypotheses, 1997, vol. 48, pp. 517-521.
Nissen et al., "Effect of Recombinant ApoA-1 Milano on Coronoary Atherosclerosis in Patients with Acute Coronary syndromes", Journal of American Medical Association, 2003, v. 290, pp. 2292-2300.
Okazaki, "Improved High-Performance Liquid Chromatographic Method for the Determination of Apolipoproteins in Serum High-Density Lipoproteins", Journal of Chromatography B: Biomedical Sciences and Applications, vol. 430, Aug. 1988, pp. 135-142.
Osborne et al., "Delipidation of Plasma Lipoproteins", Methods in Enzymology, 1986, v. 128, pp. 213-222.
Parker et al., "Plasma high density lipoprotein is increased in man when low density lipoprotein (LDL) is lowered by LDL-pheresis", Proc. Natl. Acad. Sci. USA, Feb. 1986, vol. 82, pp. 771-781.
Paterno et al., "Reconstituted High-Density Lipoprotein Exhibits Neuroprotection in Two Rat Models of Stroke", Cerebrovasc Dis., Epub Dec. 29, 2003, 17, 2-2, 204-11(Abstract only).

(56) References Cited

OTHER PUBLICATIONS

Refolo et al., "Cholesterol Metabolism: A Potential Target for Alzheimer's Disease Therapy", Neuroscience Abstracts, vol. 27, issue 2, 2001, pp. 1518, (Abstract only).

Robern et al., "The Application of Sodium Deoxycholate and Sephacryl-200 for the Delipidation and Separation of High Density Lipoproteins", Experientia, 1982, 38, 437-439.

Ryan et al., "An improved Extraction Procedure for the Determination of Triglycerides and Cholesterol in Plasma or Serum", Clinical Chemistry, vol. 13, No. 9, Sep. 1967, pp. 769-772.

Rye et al., "Changes in the Size of Reconstituted High Density Liporoteins during Incubation with Cholesteryl Ester transfer protein: The Role of Apolipoproteins", Journal of Lipid Research, vol. 33, Feb. 1992, pp. 214-224.

Scanu et al., "Solubility in Aqueous Solutions of Ethanol of the Small Molecular Weight Peptides of the Serum Very Low Density and High Density Lipoproteins: Relevance to the Recovery Problem During Delipidation of Serum Lipoproteins", Anallytical Biochemistry, 1971, 44, 576-588.

Segrest et al., "A Detailed Molecular Belt Model for Apolipoprotein A-I in Discoidal High Density Lipoprotein", Journal of Biological Chemistry, Nov. 5, 1999, 274(45), 31755-31758.

Simons et al., "Cholesterol and Alzheimer's disease: Is there a link", Neurology, 2001, 57, 1089-1093.

Slater et al., "A Comparison of Delipidated Sera Used in Studies of Sterol Synthesis by Human Mononuclear Leukocytes", J. of Lipid Research, 1979, v. 20, 413-416.

Slater et al., "The Effect of Delipidated High Density Lipoprotein on Human Leukocyte Sterol Synthesis", Atherosclerosis, 1980, 35, 41-49.

Sviridov et al., "Dynamics of Reverse Cholesterol Transport: Protection against Atherosclerosis", Atherosclerosis, vol. 161, No. 2, Apr. 2002, pp. 245-254.

Tadey et al., "Chromatographic Techniques for the Isolation and Purification of Lipoproteins", Journal of Chromatography B, 1995, v. 672, pp. 237, 253.

Thompson et al., "Plasma Exchange in the Management of Homozygous Familial Hypercholesterolaemia", Lancet (LOS), 1975, 1, 1208-1211.

Tricerri et al., "Interaction of Apolipoprotein A-1 in Three Different Conformations with Palmitoyl Oleoyl Phosphatidylcholine Vesicles", Journal of Lipid Research, 2002, v. 43, pp. 187-197.

Walker et al., "Escape from Immune System", Nature, 2000, v. 407, pp. 313-134.

Williams et al., "Low Density Lipoprotein Receptor-independent Hepatic Uptake of a Synthetic, Cholesterol-Scavenging Lipoprotein: Implications for the Treatment of Receptor-Deficient Atherosclerosis", Proc. Natl. Acad. Scci. USA, 1988, 85:242-246.

Williams et al., "Uptake of Endogenous Cholesterol by a Synthetic Lipoprotein", Biochim. Biophys. Act., Feb. 12, 1986, v. 875(2), 183-194.

Wong et al., "Retention of Gangliosides in Serum Delipidated by Diisopropyl ether-1-butanol Extraction", Journal of Lipid Research, vol. 24(5), May 1983, pp. 666-669.

Wormser, "Lipids", PSC3110—Fall Semester 2002.

Yokoyama et al., "Selective Removal of Low Density Lipoprotein by Plasmapheresis in Familial Hypercholesterolemia", Arteriosclerosis, Thrombosis, and Vascular Biology, vol. 5, Nov. 1985, pp. 613-622.

Yoshidome et al., "Serum Amyloid A and P Protein Levels are Lowered by Dextran Sulfate Cellulose Low-Density Lipoprotein Apheresis", Artificial Organs, vol. 22, Issue 2, Feb. 1998, pp. 144-148.

Zetia, http://www/zetia.com/ezetimbeizetia/hcp/product_highlights/index.jsp, Zetia (ezetimibe), Jul. 18, 2003, pp. 1-2.

Zetia, "Zetia: Compliments Statin with a Unique Mechanism", http://www.zetia.com/ezetimibeizetia.hcp/mechanism_of_actiontindex.jsp, Jul. 18, 2003, pp. 1-2.

Zhang et al., "Characterization of Phospholipids in a Pre-Alpha HDL: Selective Phospholipid Efflux with Apolipoprotein AI,-" Journal of Lipid Research, vol. 39, No. 8, Aug. 1998, pp. 1601-1607.

AHA Statistical Update, "Heart Disease and Stroke Statistics—2016 Update", Dec. 16, 2015.

Casserly et al, "Convergence of atherosclerosis and Alzheimer's disease: inflammation, cholesterol, and misfolded proteins", The Lancet, vol. 363, Apr. 3, 2004.

Office Action dated Aug. 24, 2017 for U.S. Appl. No. 15/454,263.

Radin, N. 1996 Neuromethods (vol. 7) Lipids and Related Compunds Protocol. pp. 1-61.

\* cited by examiner

METHODS FOR PRESERVING AND ADMINISTERING PRE-BETA HIGH DENSITY LIPOPROTEIN HAVING A PREDETERMINED MINIMUM LEVEL OF DEGRADATION

CROSS-REFERENCE

The present application is a continuation application of U.S. patent application Ser. No. 16/225,210, entitled "Methods for Preserving and Administering Pre-Beta High Density Lipoprotein Extracted from Human Plasma" and filed on Dec. 19, 2018, which relies on, for priority, U.S. Provisional Patent Application No. 62/611,098, entitled "Methods for Treating Cholesterol-Related Diseases" and filed on Dec. 28, 2017, both of which are herein incorporated by reference in their entirety.

FIELD

The present invention generally relates to systems, apparatus and methods for removing lipids from HDL particles while leaving LDL particles substantially intact, via the extracorporeal treatment of blood plasma using either a single solvent or multiple solvents, in order to treat chronic cardiovascular diseases and acute renal diseases. More specifically, the present invention relates to systems and methods for preserving and administering pre-β HDL from non-autologous, delipidated plasma.

BACKGROUND

Familial Hypercholesterolemia (FH) is an inherited genetic autosomal dominant disease characterized by markedly elevated low density lipoprotein (LDL), tendon xanthomas, and premature coronary heart disease, caused by mutations of "FH genes," which include the LDL-receptor (LDLR), apolipoprotein B-100 (ApoB) or proprotein convertase subtilisin/kexin type 9 (PCSK9). FH produces a clinically recognizable pattern that consists of severe hypercholesterolemia due to the accumulation of LDL in the plasma, cholesterol deposition in tendons and skin, as well as a high risk of atherosclerosis manifesting almost exclusively as coronary artery disease (CAD). In FH patients, this genetic mutation makes the liver unable to effectively metabolize (or remove) excess plasma LDL, resulting in increased LDL levels.

If an individual has inherited a defective FH gene from one parent, the form of FH is called Heterozygous FH. Heterozygous FH is a common genetic disorder, inherited in an autosomal dominant pattern, occurring in approximately 1:500 people in most countries. If the individual has inherited a defective FH gene from both parents, the form of FH is called Homozygous FH. Homozygous FH is very rare, occurring in about 1 in 160,000 to one million people worldwide, and results in LDL levels >700 mg/dl, 10 fold higher than the ideal 70 mg/dl level desired for patients with CVD. Due to the high LDL levels, patients with Homozygous FH have aggressive atherosclerosis (narrowing and blocking of blood vessels) and early heart attacks. This process starts before birth and progresses rapidly. It can affect the coronary arteries, carotid arteries, aorta, and aortic valve.

Heterozygous FH (HeFH) is normally treated with statins, bile acid sequestrants, or other lipid lowering agents that lower cholesterol levels, and/or by offering genetic counseling. Homozygous FH (HoFH) often does not respond adequately to medical therapy and may require other treatments, including LDL apheresis (removal of LDL in a method similar to dialysis), ileal bypass surgery to dramatically lower their LDL levels, and occasionally liver transplantation. A few medications have recently been approved for use by HoFH subjects. However, these medications lower LDL only, and modestly contribute to slowing, but not stopping, further progression of atherosclerosis. Additionally, these medications are known to have significant side-effects.

Cholesterol is synthesized by the liver or obtained from dietary sources. LDL is responsible for transferring cholesterol from the liver to tissues at different sites in the body. However, if LDL collects on the arterial walls, it undergoes oxidation caused by oxygen free radicals liberated from the body's chemical processes and interacts deleteriously with the blood vessels. The modified LDL causes white blood cells in the immune system to gather at the arterial walls, forming a fatty substance called plaque and injuring cellular layers that line blood vessels. The modified oxidized LDL also reduces the level of nitric oxide, which is responsible for relaxing the blood vessels and thereby allowing the blood to flow freely. As this process continues, the arterial walls slowly constrict, resulting in hardening of the arteries and thereby reducing blood flow. The gradual build-up of plaque can result in blockage of a coronary vessel and ultimately in a heart attack. The plaque build up can also occur in peripheral vessels such as the legs and this condition is known as peripheral arterial disease.

Obstructions can also appear in blood vessels that supply blood to the brain, which can result in ischemic strokes. The underlying condition for this type of obstruction is the development of fatty deposits lining the vessel walls. It is known that at least 2.7% of men and women over the age of 18 in the United States have a history of stroke. Prevalence of stroke is also known to be higher with increasing age. With the increase in the aging population, the prevalence of stroke survivors is projected to increase, especially among elderly women. A considerable portion of all strokes (at least 87%) are ischemic in nature.

Further, it has been shown that hypercholesterolemia and inflammation are two dominant mechanisms implicated in the development of atherosclerosis. There is significant overlap between vascular risk factors for both Alzheimer's disease and atherosclerosis. Inflammation has been implicated in Alzheimer's disease pathogenesis and it is suggested that abnormalities in cholesterol homeostasis may have a role as well. In addition, many of the contributory factors in atherogenesis also contribute to Alzheimer's disease. Specifically, in cell cultures, increased and decreased cholesterol levels promote and inhibit the formation of beta amyloid (Aβ) from Amyloid Precursor Protein (APP), respectively. Thus, the use of treatments with proven effects on the process of atherosclerosis may be one method for treating the progression of the Alzheimer's disease.

Another common cardiovascular disease that occurs due to development of atherosclerosis (hardening and narrowing of the arteries) within the elastic lining inside a coronary artery, is Coronary Artery Disease (CAD), also known as Ischemic Heart Disease (IHD). On the basis of a statistical data collected from 2009 to 2012, an estimated 15.5 million Americans ≥20 years of age have CAD. The total CAD prevalence in the United States is 6.2% of adults ≥20 years of age.

An acute decrease in blood flow in the coronary arteries may result in part of the heart muscle unable to function properly. This condition is known as Acute Coronary Syndrome (ACS). A conservative estimate for the number of hospital discharges with ACS in 2010 is 625,000.

In contrast to LDL, high plasma HDL levels are desirable because they play a major role in "reverse cholesterol transport", where the excess cholesterol is transferred from tissue sites to the liver where it is eliminated. Optimal total cholesterol levels are 200 mg/dl or below with a LDL cholesterol level of 160 mg/dl or below and a HDL-cholesterol level of 45 mg/dl for men and 50 mg/dl for women. Lower LDL levels are recommended for individuals with a history of elevated cholesterol, atherosclerosis or coronary artery disease. High levels of LDL increase the lipid content in coronary arteries resulting in formation of lipid filled plaques that are vulnerable to rupture. On the other hand, HDL has been shown to decrease the lipid content in the lipid filled plaques, reducing the probability of rupture. In the last several years, clinical trials of low density lipoprotein (LDL)-lowering drugs have definitively established that reductions in LDL are associated with a 30-45% decrease in clinical cardiovascular disease (CVD) events. CVD events include events occurring in diseases such as HoFH, HeFH, and peripheral arterial disease. Despite lowered LDL, however, many patients continue to have cardiac events. Low levels of HDL are often present in high risk subjects with CVD, and epidemiological studies have identified HDL as an independent risk factor that modulates CVD risk. In addition to epidemiologic studies, other evidence suggests that raising HDL would reduce the risk of CVD. There has been increasing interest in changing plasma HDL levels by dietary, pharmacological or genetic manipulations as a potential strategy for the treatment of CVD including HoFH, HeFH, Ischemic stroke, CAD, ACS, and peripheral arterial disease and for treating the progression of Alzheimer's Disease.

The protein component of LDL, known as apolipoprotein-B (ApoB), and its products, comprise atherogenic elements. Elevated plasma LDL levels and reduced HDL levels are recognized as primary causes of coronary disease. ApoB is in highest concentration in LDL particles and is not present in HDL particles. Apolipoprotein A-I (ApoA-I) and apolipoprotein A-II (ApoA-II) are found in HDL. Other apolipoproteins, such as ApoC and its subtypes (C-I, C-II and C-III), ApoD, and ApoE are also found in HDL. ApoC and ApoE are also observed in LDL particles.

Numerous major classes of HDL particles including HDL2b, HDL2a, HDL3a, HDL3b and HDL3 have been reported. Various forms of HDL particles have been described on the basis of electrophoretic mobility on agarose as two major populations, a major fraction with $\alpha$-HDL mobility and a minor fraction with migration similar to VLDL. This latter fraction has been called pre-$\beta$ HDL and these particles are the most efficient HDL particle subclass for inducing cellular cholesterol efflux.

The HDL lipoprotein particles are comprised of ApoA-I, phospholipids and cholesterol. The pre-$\beta$ HDL particles are considered to be the first acceptors of cellular free cholesterol and are essential in eventually transferring free and esterified cholesterol to $\alpha$-HDL. Pre-$\beta$ HDL particles may transfer cholesterol to $\alpha$-HDL or be converted to $\alpha$-HDL. The alpha HDL transfers cholesterol to the liver, where excess cholesterol can be removed from the body.

HDL levels are inversely correlated with atherosclerosis and coronary artery disease. Once cholesterol-carrying $\alpha$-HDL reaches the liver, the $\alpha$-HDL particles divest of the cholesterol and transfer the free cholesterol to the liver. The $\alpha$-HDL particles (divested of cholesterol) are subsequently converted to pre-$\beta$ HDL particles and exit the liver, which then serve to pick up additional cholesterol within the body and are converted back to $\alpha$-HDL, thus repeating the cycle. Accordingly, what is needed is a method to decrease or remove cholesterol from these various HDL particles, especially the $\alpha$-HDL particles, so that they are available to remove additional cholesterol from cells.

Renal arterial stenosis refers to a blockage in an artery that supplies blood to the kidney and is characterized in two forms: a) smooth muscle plaque or b) cholesterol filled plaque. This condition, generally known as renal arterial stenosis, decreases blood flow to the kidney and can result in high blood pressure. Plaque in the renal arteries may be discovered during a CT angiogram. In some cases, renal arterial stenosis is discovered while performing a CT angiogram for an aortic aneurysm. Conventionally, blood pressure increases gradually with age. However, a sudden onset of hypertension is also likely to be associated with renal obstruction or renal arterial stenosis. A decrease in flow of blood to the kidney causes vasoconstriction or high blood pressure, as the kidney starts producing an excess of cytokines.

In addition, a "cholesterol embolism', can occur when the cholesterol in the artery is released, usually from an atherosclerotic plaque, and travels as an embolus in the bloodstream causing an obstruction (as an embolism) in blood vessels that are positioned further away. Once in circulation, the cholesterol particles get stuck in tiny blood vessels, or arterioles. They can reduce blood flow to tissues and cause inflammation and tissue damage that can harm the kidneys. A cholesterol embolism may result in renal failure, and is a disease state referred to as Atheroembolic Renal Disease (AERD). AERD is one of the manifestations of diseases that may occur due to a cholesterol-filled plaque. In a patient with AERD, the plaque may rupture in the artery and release the cholesterol and other "junk" within the plaque into the vessel. The released cholesterol and junk may travel down the artery and may block the artery and injure a part of the kidney and its tissues, thereby resulting in AERD. Atherosclerosis of the aorta is the most common cause of AERD.

Currently, treatment of renal arterial stenosis, its manifestations such as AERD, and other cardiovascular diseases involves putting a stent in an artery to open the vessel. This technique often normalizes the blood pressure. However, installing a stent is likely to only treat the symptoms, such as high blood pressure. There are also instances when the blood pressure is normal, but AERD is present in a patient. There is thus a need to address the underlying cause of the disease, and treat renal arterial stenosis either in combination with or independently of high blood pressure symptoms.

Hyperlipidemia (or abnormally high concentration of lipids in the blood) may be treated by changing a patient's diet. However, diet as a primary mode of therapy requires a major effort on the part of patients, physicians, nutritionists, dietitians, and other health care professionals and thus undesirably taxes the resources of health professionals. Another negative aspect of this therapy is that its success does not rest exclusively on diet. Rather, success of dietary therapy depends upon a combination of social, psychological, economic, and behavioral factors. Thus, therapy based only on correcting flaws within a patient's diet, is not always successful.

In instances when dietary modification has been unsuccessful, drug therapy has been used as adjunctive therapy. Such therapy has included use of commercially available hypolipidemic drugs administered alone or in combination with other therapies as a supplement to dietary control. These drugs, called statins, include lovastatin, pravastatin, simvastatin, fluvastatin, atorvastatin, and cerivastatin. Statins are particularly effective for lowering LDL levels and are also effective in the reduction of triglycerides, apparently in direct proportion to their LDL-lowering effects. Statins raise HDL levels, but to a lesser extent than other anti-cholesterol drugs. Statins also increase nitric oxide, which, as described above, is reduced in the presence of oxidized LDL.

Bile acid resins, another drug therapy, work by binding with bile acid, a substance made by the liver using cholesterol as one of the primary manufacturing components. Because the drugs bind with bile acids in the digestive tract, they are then excreted with the feces rather than being absorbed into the body. The liver, as a result, must take more cholesterol from the circulation to continue constructing bile acids, resulting in an overall decrease in LDL levels.

Nicotinic acid, or niacin, also known as vitamin B3, is effective in reducing triglyceride levels and raising HDL levels higher than any other anti-cholesterol drug. Nicotinic acid also lowers LDL-cholesterol.

Fibric acid derivatives, or fibrates, are used to lower triglyceride levels and increase HDL when other drugs ordinarily used for these purposes, such as niacin, are not effective.

Probucol lowers LDL-cholesterol levels, however, it also lowers HDL levels. It is generally used for certain genetic disorders that cause high cholesterol levels, or in cases where other cholesterol-lowering drugs are ineffective or cannot be used.

PCSK9s lower LDL-cholesterol levels via increasing the cellular level of LDL receptors that reside in the liver.

Hypolipidemic drugs have had varying degrees of success in reducing blood lipid; however, none of the hypolipidemic drugs successfully treats all types of hyperlipidemia. While some hypolipidemic drugs have been fairly successful, the medical community has found little conclusive evidence that hypolipidemic drugs cause regression of atherosclerosis. In addition, all hypolipidemic drugs have undesirable side effects. As a result of the lack of success of dietary control, drug therapy and other therapies, atherosclerosis remains a major cause of death in many parts of the world.

New therapies have been used to reduce the amount of lipid in patients for whom drug and diet therapies were not sufficiently effective. For example, extracorporeal procedures like plasmapheresis and LDL-apheresis have been employed and are shown to be effective in lowering LDL.

Plasmapheresis therapy or plasma exchange therapy, involves replacing a patient's plasma with donor plasma or more usually a plasma protein fraction. Plasmapheresis is a process whereby the blood plasma is removed from blood cells by a cell separator. The separator works either by spinning the blood at high speed to separate the cells from the fluid or by passing the blood through a membrane with pores so small that only the fluid component of the blood can pass through. The cells are returned to the person undergoing treatment, while the plasma is discarded and replaced with other fluids.

This treatment has resulted in complications due to the introduction of foreign proteins and transmission of infectious diseases. Further, plasmapheresis has the disadvantage of non-selective removal of all serum lipoproteins, such as VLDL, LDL, and HDL. Moreover, plasmapheresis can result in several side effects including allergic reactions in the form of fever, chills, and rash and possibly even anaphylaxis.

As described above, it is not desirable to remove HDL, which is secreted from both the liver and the intestine as nascent, disk-shaped particles that contain cholesterol and phospholipids. HDL is believed to play a role in reverse cholesterol transport, which is the process by which excess cholesterol is removed from tissues and transported to the liver for reuse or disposal in the bile.

In contrast to plasmapheresis, the LDL-apheresis procedure selectively removes ApoB containing cholesterol, such as LDL, while retaining HDL. Several methods for LDL-apheresis have been developed. These techniques include absorption of LDL in heparin-agarose beads, the use of immobilized LDL-antibodies, cascade filtration absorption to immobilize dextran sulfate, and LDL precipitation at low pH in the presence of heparin. Each method described above is effective in removing LDL. This treatment process has disadvantages, however, including the failure to positively affect HDL or to cause a metabolic shift that can enhance atherosclerosis and other cardiovascular diseases. LDL apheresis, as its name suggests, merely treats LDL in patients with severe hyperlipidemia.

Yet another method of achieving a reduction in plasma cholesterol in homozygous familial hypercholesterolemia, heterozygous familial hypercholesterolemia and patients with acquired hyperlipidemia is an extracorporeal lipid elimination process, referred to as cholesterol apheresis. In cholesterol apheresis, blood is withdrawn from a patient, the plasma is separated from the blood, and the plasma is mixed with a solvent mixture. The solvent mixture extracts lipids from the plasma. Thereafter, the delipidated plasma is recombined with the patient's blood cells and returned to the patient. Using this procedure, however, results in a modification of the LDL particles, such that the modified LDL particles could result in increased intensity of the heart disease. At the same time, this process also resulted in further delipidation of the HDL particles.

Conventional extracorporeal delipidation processes, however, are directed toward the concurrent delipidation of LDL and HDL. This process can have a number of disadvantages. The main disadvantage being that delipidated LDL tends to aggregate and subsequently cause an increase in heart disease conditions, rather than decrease. In addition, extracorporeal systems are designed to subject body fluid volumes to substantial processing, possibly through multiple stage solvent exposure and extraction steps.

Vigorous multi-stage solvent exposure and extraction can have several drawbacks. It may be difficult to remove a sufficient amount of solvents from the delipidated plasma in order for the delipidated plasma to be safely returned to a patient.

Hence, existing apheresis and extracorporeal systems for treatment of plasma constituents suffer from a number of disadvantages that limit their ability to be used in clinical applications. A need exists for improved systems, apparatuses and methods capable of removing lipids from blood components in order to provide treatments and preventative measures for chronic cardiovascular diseases. Methods have also been provided to selectively remove lipid from HDL particles and thereby create modified HDL particles with increased capacity to accept cholesterol.

Methods have been provided to selectively remove lipid from HDL particles and thereby create modified HDL particles with increased capacity to accept cholesterol, without substantially affecting LDL particles, in chronic diseases. However, these methods envision the immediate re-administration of the modified HDL particles and do not provide any means to preserve, store, or otherwise use the modified HDL particles over longer periods of time.

What is also needed is a method to preserve delipidated plasma and the modified HDL particles. Plasma derived from autologous and non-autologous sources are required to be introduced to a patient within a few hours of the derivation. However, there are situations when it may not be possible to introduce derived modified HDL particles within the stipulated time period of the derivation to a patient. This may particularly be true in cases where a patient needs modified HDL particles that cannot be sufficiently derived from the patient (autologous), but rather, non-autologous plasma sources are available. Access to life-saving therapy for more patients may be enhanced by preserving and making delipidated plasma readily available, so that it can be used as and when required.

SUMMARY

The following embodiments and aspects thereof are described and illustrated in conjunction with systems, tools and methods, which are meant to be exemplary and illustrative, not limiting in scope.

A method for preserving pre-beta high density lipoprotein for administration to a patient, comprising: obtaining a batch of delipidated plasma comprising the pre-beta high density lipoprotein; testing a portion of the batch of the delipidated plasma to characterize the pre-beta high density lipoprotein; preserving the batch of the delipidated plasma; preparing the preserved delipidated plasma for administration to the patient; testing the prepared delipidated plasma to characterize the pre-beta high density lipoprotein; and administering the pre-beta high density lipoprotein to the patient.

Optionally, the method further comprises, prior to preserving, modifying an amount of the pre-beta high density lipoprotein to insure a concentration of the pre-beta high density lipoprotein is in a range of 1 mg/dl to 400 mg/dl.

Optionally, preserving comprises freezing the batch at a temperature less than −30° C.

Optionally, preparing comprises thawing the preserved delipidated plasma in a temperature range of 2° C. to 26° C.

Optionally, preserving comprises subjecting a volume of delipidated plasma in a range from 1 milliliter to 2 liters to a temperature less than −30° C. for less than 20 minutes.

Optionally, testing the portion of the batch of the delipidated plasma to characterize the pre-beta high density lipoprotein comprises determining a first concentration of the pre-beta high density lipoprotein. Optionally, testing the prepared delipidated plasma to characterize the pre-beta high density lipoprotein comprises determining a second concentration of the pre-beta high density lipoprotein and comparing the second concentration of the pre-beta high density lipoprotein to the first concentration of the pre-beta high density lipoprotein to determine an extent of degradation. Optionally, the method further comprises determining if the prepared delipidated plasma is suitable for administration based on the second concentration of the pre-beta high density lipoprotein.

Optionally, the method further comprises, prior to preservation, adding a preservative to the delipidated plasma.

Optionally, preparing comprises thawing the preserved delipidated plasma and further comprising storing the thawed delipidated plasma at a temperature in a range of 1° C. to 6° C. for no more than 5 days.

The present specification also discloses a method for preserving modified high density lipoproteins for administration to a patient, comprising: obtaining a batch of delipidated plasma comprising the modified high density lipoproteins by connecting at least one person to a device for withdrawing blood, withdrawing blood containing blood cells from the at least one person, separating the blood cells from the blood to yield a blood plasma fraction containing high density lipoproteins and low density lipoproteins, delipidating the high density lipoproteins using a solvent, separating out the low density lipoproteins, and collecting the delipidated plasma with the modified high density lipoproteins; testing a portion of the batch of the delipidated plasma to characterize the modified high density lipoproteins; preserving the batch of the delipidated plasma; preparing the preserved delipidated plasma for administration to the patient; testing the prepared delipidated plasma to characterize the modified high density lipoproteins; and administering the modified high density lipoproteins to the patient.

Optionally, the method further comprises, prior to preserving, modifying an amount of the modified high density lipoproteins to insure a concentration of the modified high density lipoproteins is in a range of 1 mg/dl to 400 mg/dl.

Optionally, preserving comprises freezing the batch at a temperature less than −30° C.

Optionally, preparing comprises thawing the preserved delipidated plasma in a temperature range of 2° C. to 26° C.

Optionally, preserving comprises subjecting a volume of delipidated plasma in a range from 1 milliliter to 2 liters to a temperature less than −30° C. for less than 20 minutes.

Optionally, testing the portion of the batch of the delipidated plasma to characterize the modified high density lipoproteins comprises determining a first concentration of the modified high density lipoproteins. Optionally, testing the prepared delipidated plasma to characterize the modified high density lipoproteins comprises determining a second concentration of the modified density lipoproteins and comparing the second concentration of the modified high density lipoproteins to the first concentration of the modified density lipoproteins to determine an extent of degradation. Optionally, the method further comprises determining if the prepared delipidated plasma is suitable for administration based on the second concentration of the modified high density lipoproteins.

Optionally, the method further comprises, prior to preservation, adding a preservative to the delipidated plasma.

Optionally, preparing comprises thawing the preserved delipidated plasma and further comprising storing the thawed delipidated plasma at a temperature in a range of 1° C. to 6° C. for no more than 5 days.

The present specification also discloses a method for treatment of cardiovascular disease in a patient, comprising: obtaining a blood plasma fraction containing high density lipoprotein and low density lipoprotein; mixing the plasma fraction with a lipid removing agent which removes lipids to yield a mixture of lipid, the lipid removing agent, modified high density lipoprotein, and the low density lipoprotein, wherein the modified high density lipoprotein is a delipidated high density lipoprotein; separating the modified high density lipoprotein and the low density lipoprotein from the lipid and the lipid removing agent; preserving the modified high density lipoprotein for a prolonged period of time; preparing for use the preserved modified high density lipoprotein; separating components of high density lipoprotein particles from the modified high density lipoprotein prepared after preservation; and delivering the components of high density lipoprotein particles to the patient.

Optionally, the method of preserving comprises freezing. Optionally, the method of preparing for use comprises thawing.

Optionally, the method of preserving comprises preserving a volume of DP ranging from 1 milliliter to 2 liters.

Optionally, the method of mixing comprises mixing the blood plasma fraction with a lipid removing agent which removes lipids associated with the high density lipoprotein without substantially modifying the low density lipoprotein.

Optionally, the method of obtaining a blood plasma fraction containing high density lipoprotein and low density lipoprotein comprises obtaining from at least one of the patient or an individual other than the patient.

Optionally, the method for treatment of cardiovascular disease includes treating at least one of AERD, Homozygous Familial Hypercholesterolemia Heterozygous Familial Hypercholesterolemia, Ischemic stroke, Coronary Artery Disease, Acute Coronary Syndrome, and peripheral arterial disease.

Optionally, the method for treatment of cardiovascular diseases includes method for treatment of a progression of Alzheimer's disease.

Optionally, the step of mixing the blood plasma fraction with a lipid removing agent yields modified high density lipoprotein that has an increased concentration of pre-beta high density lipoprotein relative to total protein.

Optionally, the step of obtaining a blood plasma fraction from treating cardiovascular diseases further comprises: connecting a person to a device for withdrawing blood; withdrawing blood containing blood cells from the person; and separating the blood cells from the blood to yield a blood plasma fraction containing high density lipoprotein and low density lipoprotein.

Optionally, the step of separating components of high density lipoprotein particles from the modified high density lipoprotein comprises using affinity chromatography.

Optionally, the method of using affinity chromatography comprises: adding the plasma containing delipidated high density lipoprotein to a column; allowing the plasma to drip through the column wherein the column contains an antibody for binding to ApoA-I protein; washing the column to remove any unwanted material; and delivering a disassociating reagent through the column to break a bond between the antibody and ApoA-I protein, thereby separating at least pre-beta HDL.

Optionally, the step of separating components of high density lipoprotein particles from the modified high density lipoprotein comprises using ultracentrifugation.

Optionally, using ultracentrifugation comprises: spinning the modified high density lipoprotein at a density of 1.21; separating out a bottom fraction containing pre-beta high density lipoprotein particles and plasma proteins; and spinning the bottom fraction at a density of 1.25 to separate pre-beta high density lipoprotein particles from plasma proteins.

Optionally, using ultracentrifugation comprises: spinning the modified high density lipoprotein at a density of 1.006; separating bottom fraction containing plasma with low density lipoprotein and high density lipoprotein; spinning the separated plasma with low density lipoprotein and high density lipoprotein at a density of 1.063; separating out a bottom fraction containing high density lipoprotein particles; spinning the separated high density lipoprotein particles at a density of 1.21; separating out a bottom fraction containing pre-beta high density lipoprotein particles and plasma proteins; and spinning the bottom fraction at a density of 1.25 to separate pre-beta high density lipoprotein particles from plasma proteins.

Optionally, using ultracentrifugation comprises: spinning the modified high density lipoprotein at a density of 1.063; separating out a bottom fraction containing alpha and pre-beta high density lipoprotein particles and plasma proteins; and spinning the bottom fraction at a density of 1.25 to separate alpha and pre-beta high density lipoprotein particles from plasma proteins.

The present specification also discloses a method for treatment of cardiovascular disease in a patient, comprising: obtaining a blood plasma fraction containing high density lipoprotein and low density lipoprotein; mixing the plasma fraction with a lipid removing agent which removes lipids to yield a mixture of lipid, the lipid removing agent, modified high density lipoprotein, and the low density lipoprotein, wherein the modified high density lipoprotein is a delipidated high density lipoprotein; separating the modified high density lipoprotein and the low density lipoprotein from the lipid and the lipid removing agent; separating components of high density lipoprotein particles from the modified high density lipoprotein; preserving the components of high density lipoprotein particles for a prolonged period of time; preparing for use the preserved components of high density lipoprotein particles; and delivering the components of high density lipoprotein particles to the patient.

The present specification also discloses a method for treatment of cardiovascular disease in a patient, comprising: obtaining a blood plasma fraction containing high density lipoprotein and low density lipoprotein; mixing the plasma fraction with a lipid removing agent which removes lipids to yield a mixture of lipid, the lipid removing agent, modified high density lipoprotein, and the low density lipoprotein, wherein the modified high density lipoprotein is a delipidated high density lipoprotein; separating the modified high density lipoprotein and the low density lipoprotein from the lipid and the lipid removing agent; separating components of high density lipoprotein particles from the modified high density lipoprotein; and preserving the components of high density lipoprotein particles for a prolonged period of time.

Optionally, the method further comprises preparing for use the preserved components of high density lipoprotein particles.

Optionally, the method further comprises delivering the components of high density lipoprotein particles to the patient.

Optionally, the step of preservation comprises freezing.

Optionally, the step of preparing comprises thawing.

Optionally, the components of high density lipoprotein particles comprise alpha high density lipoprotein and/or pre-beta high density lipoprotein.

Optionally, the components of high density lipoprotein particles comprise pre-beta high density lipoprotein.

The present specification also discloses a method for treatment of cardiovascular disease in a patient, comprising: obtaining a blood plasma fraction containing high density lipoprotein and low density lipoprotein; mixing the plasma fraction with a lipid removing agent which removes lipids to yield a mixture of lipid, the lipid removing agent, modified high density lipoprotein, and the low density lipoprotein, wherein the modified high density lipoprotein is a delipidated high density lipoprotein; separating the modified high density lipoprotein and the low density lipoprotein from the lipid and the lipid removing agent; preserving the modified high density lipoprotein for a predetermined or prolonged period of time; preparing for use the preserved modified high density lipoprotein; separating components of high density lipoprotein particles from the modified high density lipoprotein prepared after preservation; preserving the components of high density lipoprotein particles for a prolonged or predetermined period of time; preparing for use the preserved components of high density lipoprotein particles; and delivering the components of high density lipoprotein particles to the patient.

Optionally, the preserving comprises freezing.

Optionally, the preparing comprises thawing.

Optionally, the components of high density lipoprotein particles comprise alpha high density lipoprotein and/or pre-beta high density lipoprotein.

Optionally, the components of high density lipoprotein particles comprise pre-beta high density lipoprotein.

The aforementioned and other embodiments of the present specification shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION

Figure 1A:
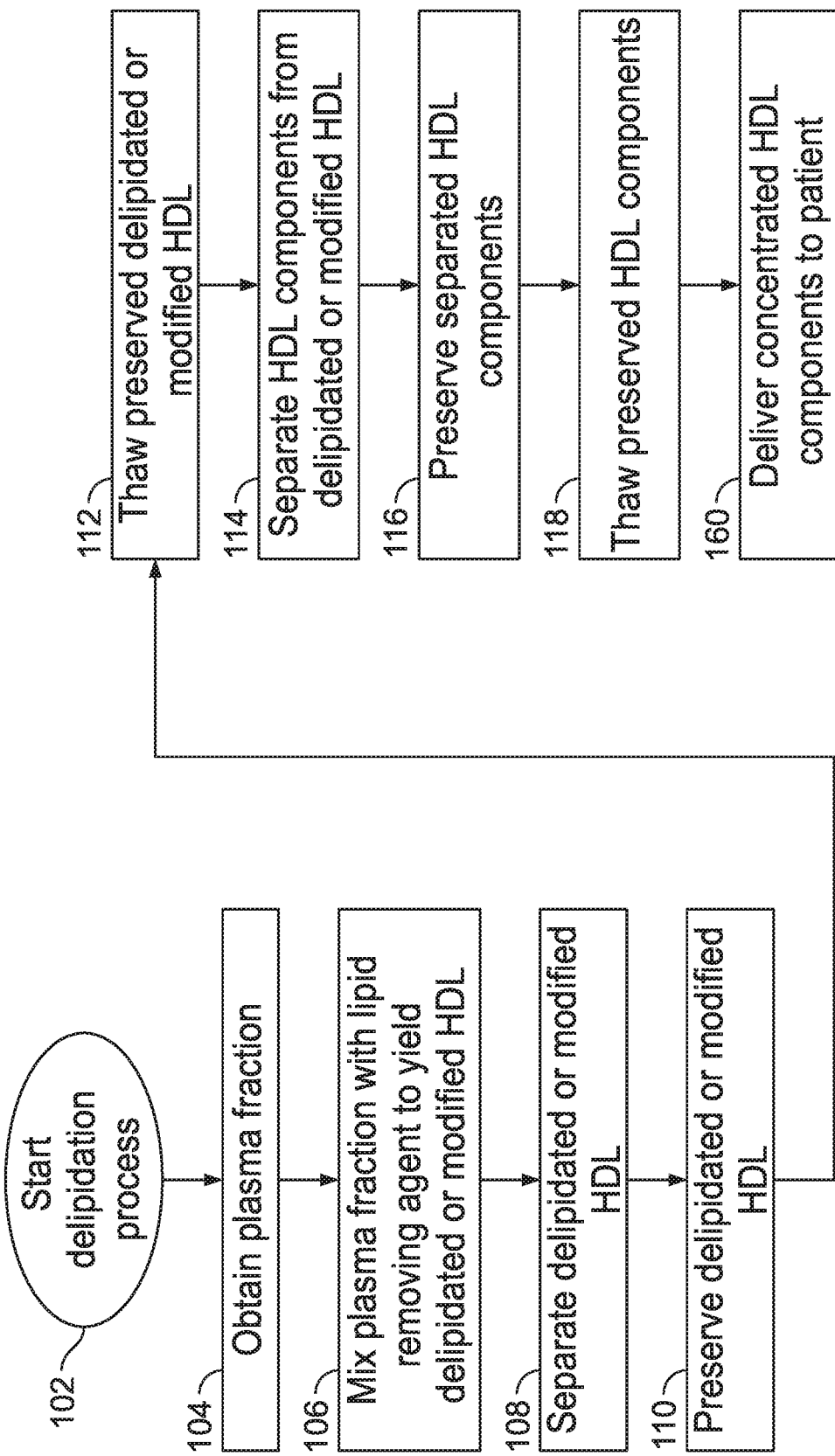
FIG. 1A is a flow chart illustrating an exemplary process for separating pre-beta HDL from delipidated (modified) HDL, in accordance with some embodiments of the present specification.

In some embodiments, the present specification is directed towards systems, apparatuses and methods for preserving modified HDL particles (also referred to as delipidated HDL) with reduced lipid content, particularly reduced cholesterol content derived primarily from plasma of non-autologous sources for a patient, where the preserved product may be for later use. Embodiments of the present specification create and preserve these modified HDL particles with reduced lipid content without substantially modifying LDL particles. Embodiments of the present specification modify original α-HDL particles (present in delipidated plasma) to yield modified HDL particles that have an increased concentration of components of HDL, including α-HDL and/or pre-β HDL relative to the original HDL. Further, the newly formed derivatives of HDL particles (modified HDL) are treated to separate α-HDL and/or pre-β HDL, from the delipidated plasma. In some embodiments, delipidated plasma is treated to create an even more concentrated solution of α-HDL and/or pre-β HDL. The modified HDL, with a concentrated solution of α-HDL and/or pre-β HDL is preserved, in an embodiment, by freezing and administered to the patient at a later time after thawing the preserved modified HDL, in order to enhance cellular cholesterol efflux and treat cardiovascular diseases and/or other lipid-associated diseases. In an embodiment, the modified HDL contains a concentrated solution of approximately 20% α-HDL particles (present in delipidated plasma) and approximately 80% pre-β HDL.

The treatment processes of the present specification renders the methods and systems of the present specification more effective in treating cardiovascular diseases including Homozygous Familial Hypercholesterolemia (HoFH), Heterozygous Familial Hypercholesterolemia (HeFH), Ischemic stroke, Coronary Artery Disease (CAD), Acute Coronary Syndrome (ACS), peripheral arterial disease (PAD), AERD, Renal Arterial Stenosis (RAS) and its manifestations, and for treating the progression of Alzheimer's Disease.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention. In the description and claims of the application, each of the words "comprise" "include" and "have", and forms thereof, are not necessarily limited to members in a list with which the words may be associated.

It should be noted herein that any feature or component described in association with a specific embodiment may be used and implemented with any other embodiment unless clearly indicated otherwise.

The term "fluid" may be defined as fluids from animals or humans that contain lipids or lipid containing particles, fluids from culturing tissues and cells that contain lipids and fluids mixed with lipid-containing cells. For purposes of this invention, decreasing the amount of lipids in fluids includes decreasing lipids in plasma and particles contained in plasma, including but not limited to HDL particles. Fluids include, but are not limited to: biological fluids; such as blood, plasma, serum, lymphatic fluid, cerebrospinal fluid, peritoneal fluid, pleural fluid, pericardial fluid, various fluids of the reproductive system including, but not limited to, semen, ejaculatory fluids, follicular fluid and amniotic fluid;

cell culture reagents such as normal sera, fetal calf serum or serum derived from any animal or human; and immunological reagents, such as various preparations of antibodies and cytokines from culturing tissues and cells, fluids mixed with lipid-containing cells, and fluids containing lipid-containing organisms, such as a saline solution containing lipid-containing organisms. A preferred fluid treated with the methods of the present invention is plasma.

The term "lipid" may be defined as any one or more of a group of fats or fat-like substances occurring in humans or animals. The fats or fat-like substances are characterized by their insolubility in water and solubility in organic solvents. The term "lipid" is known to those of ordinary skill in the art and includes, but is not limited to, complex lipid, simple lipid, triglycerides, fatty acids, glycerophospholipids (phospholipids), true fats such as esters of fatty acids, glycerol, cerebrosides, waxes, and sterols such as cholesterol and ergosterol.

The term "extraction solvent" may be defined as one or more solvents used for extracting lipids from a fluid or from particles within the fluid. This solvent enters the fluid and remains in the fluid until removed by other subsystems. Suitable extraction solvents include solvents that extract or dissolve lipid, including but not limited to phenols, hydrocarbons, amines, ethers, esters, alcohols, halohydrocarbons, halocarbons, and combinations thereof. Examples of suitable extraction solvents are ethers, esters, alcohols, halohydrocarbons, or halocarbons which include, but are not limited to di-isopropyl ether (DIPE), which is also referred to as isopropyl ether, diethyl ether (DEE), which is also referred to as ethyl ether, lower order alcohols such as butanol, especially n-butanol, ethyl acetate, dichloromethane, chloroform, isoflurane, sevoflurane (1,1, 1,3, 3,3-hexafluoro-2-(fluoromethoxy) propane-d3), perfluorocyclohexanes, trifluoroethane, cyclofluorohexanol, and combinations thereof.

The term "patient" refers to animals and humans, which may be either a fluid source to be treated with the methods of the present invention or a recipient of derivatives of HDL particles and or plasma with reduced lipid content.

The term "HDL particles" encompasses several types of particles defined based on a variety of methods such as those that measure charge, density, size and immuno-affinity, including but not limited to electrophoretic mobility, ultra-centrifugation, immunoreactivity and other methods known to one of ordinary skill in the art. Such HDL particles include but are not limited to the following: α-HDL, pre-β HDL (including pre-β1 HDL, pre-β2 HDL and pre-(β3HDL), HDL2 (including HDL2a and HDL2b), HDL3, VHDL, LpA-I, LpA-II, LpA-I/LpA-II (for a review see Barrans et al., Biochemica Biophysica Acta 1300; 73-85, 1996). Accordingly, practice of the methods of the present invention creates modified HDL particles. These modified derivatives of HDL particles may be modified in numerous ways including but not limited to changes in one or more of the following metabolic and/or physico-chemical properties (for a review see Barrans et al., Biochemica Biophysica Acta 1300; 73-85, 1996); molecular mass (kDa); charge; diameter; shape; density; hydration density; flotation characteristics; content of cholesterol; content of free cholesterol; content of esterified cholesterol; molar ratio of free cholesterol to phospholipids; immuno-affinity; content, activity or helicity of one or more of the following enzymes or proteins: ApoA-I, ApoA-II, ApoD, ApoE, ApoJ, ApoA-IV, cholesterol ester transfer protein (CETP), lecithin; cholesterol acyltransferase (LCAT); capacity and/or rate for cholesterol binding, capacity and/or rate for cholesterol transport.

The terms "modified high density lipoprotein" and "delipidated high density lipoprotein" may be used interchangeably and refer to reduced lipid blood products, and in particular, high density lipoproteins having a reduced lipid content, that may be contained within the resultant plasma once a delipidation process has been performed. Similarly, the term "treated plasma" refers to the resultant plasma once a delipidation process has been performed.

FIG. 1A is a flow chart illustrating an exemplary process for separating pre-beta HDL from modified HDL, in accordance with some embodiments of the present specification. At 102, a plasma delipidation process is started for a subject or a patient who is suffering from a cardiovascular or a related disease. The process is typically started after one or more observations made by a physician treating the patient. The observations may be based on a combination of symptoms and test-results such as but not limited to from blood tests and imaging-analyses. The observation may lead the physician to conclude that treatment for the patient requires reduction of harmful lipids from the patient's physiological system.

At 104, a blood fraction is obtained, which in an embodiment, is plasma. In accordance with embodiments of the present specification, the blood fraction is obtained from either the patient (autologous) or from a non-autologous source. The blood fraction from the non-autologous source is collected from healthy, voluntary donors. The process of blood fractionation is typically done by filtration, centrifuging the blood, aspiration, or any other method known to persons skilled in the art. Blood fractionation separates the plasma from the blood. In an embodiment, blood fractionation is performed remotely from the method described in context of FIG. 1A. In one embodiment, blood is withdrawn from a patient or a donor in a volume sufficient to produce about 12 ml/kg of plasma based on body weight. During the fractionation process, the blood can optionally be combined with an anticoagulant, such as sodium citrate, and centrifuged at forces approximately equal to 2,000 times gravity. The blood is separated into plasma and red blood cells using methods commonly known to one of skill in the art, such as plasmapheresis. In an embodiment, the red blood cells are then aspirated from the plasma. In one embodiment, the process of blood fractionation is performed by withdrawing blood from the patient with the cardiovascular and/or related disease, and who is being treated by the physician. In an alternative embodiment, the process of blood fractionation is performed by withdrawing blood from a person other than the patient with the cardiovascular and/or related disease who is treated by the physician. Therefore, the plasma obtained as a result of the blood fractionation process may be either autologous or non-autologous.

Subsequent to fractionation, the red blood cells are either stored in an appropriate storage solution or, preferably, returned to the patient during plasmapheresis. Physiological saline may also optionally be administered to the patient to replenish volume. If the blood was obtained from an individual other than the patient, the cells are returned to that individual, who can also be referred to as the donor.

Plasma obtained from blood is usually a straw-colored liquid that comprises the extracellular matrix of blood cells. Plasma is typically 95% water, and contains dissolved proteins, which constitute about 6-8% of plasma. The plasma also contains glucose, clotting factors, electrolytes, hormones, carbon dioxide, and oxygen. The plasma has a density of approximately 1006 kg/m3, or 1.006 g/ml.

In some alternate embodiments, Low Density Lipoprotein (LDL) is also separated from the plasma. Separated LDL is usually discarded. In alternative embodiments, LDL is retained in the plasma. In accordance with embodiments of the present specification, blood fraction or plasma obtained at 104 includes plasma with High Density Lipoprotein (HDL), and may or may not include other protein particles. In embodiments, autologous or non-autologous plasma collected from the patient or donor, respectively, is subsequently isolated via an approved plasmapheresis device. The plasma may be transported using a continuous or batch process.

At 106, the blood fraction or plasma obtained at 104 is mixed with one or more solvents, such as lipid removing agents. In an embodiment, the solvents used include either or both of organic solvents sevoflurane and n-butanol. In embodiments, the plasma and solvent are introduced into at least one apparatus for mixing, agitating, or otherwise contacting the plasma with the solvent. In embodiments, the solvent system is optimally designed such that only the HDL particles are treated to reduce their lipid levels and LDL levels are not affected. The solvent system includes factoring in variables such as the solvent employed, mixing method, time, and temperature. Solvent type, ratios and concentrations may vary in this step. Acceptable ratios of solvent to plasma include any combination of solvent and plasma. In some embodiments, ratios used are 2 parts plasma to 1 part solvent, 1 part plasma to 1 part solvent, or 1 part plasma to 2 parts solvent. In an embodiment, when using a solvent comprising 95 parts sevoflurane to 5 parts n-butanol, a ratio of two parts solvent per one part plasma is used. Additionally, in an embodiment employing a solvent containing n-butanol, the present specification uses a ratio of solvent to plasma that yields at least 3% n-butanol in the final solvent/plasma mixture. In an embodiment, a final concentration of n-butanol in the final solvent/plasma mixture is 3.33%. The plasma and solvent are introduced into at least one apparatus for mixing, agitating, or otherwise contacting the plasma with the solvent. The plasma may be transported using a continuous or batch process. Further, various sensing means may be included to monitor pressures, temperatures, flow rates, solvent levels, and the like. The solvents dissolve lipids from the plasma. In embodiments of the present specification, the solvents dissolve lipids to yield treated plasma that contains modified HDL particles with reduced lipid content. The process is designed such that HDL particles are treated to reduce their lipid levels and yield modified HDL particles without destruction of plasma proteins or substantially affecting LDL particles. It should be noted that there is no clinically significant decrease in blood constituents post-plasmapheresis.

Energy is introduced into the system in the form of varied mixing methods, time, and speed. At 108, bulk solvents are removed from the modified HDL particles via centrifugation. In embodiments, any remaining soluble solvent is removed via charcoal adsorption, evaporation, or Hollow Fiber Contractors (HFC) pervaporation. The mixture is optionally tested for residual solvent via use of Gas Chromatography (GC), or similar means. The test for residual solvent may optionally be eliminated based on statistical validation.

The extracted modified HDL solution has an increased concentration of pre-beta HDL. It is estimated that the modified HDL in the delipidated plasma, has approximately 80-85% of pre-β particles, and about 15-20% of α HDL particles. Concentration of pre-beta HDL is greater in the modified HDL, relative to the original HDL that was present in the plasma before treating it with the solvent. Compared to the plasma solution originally separated from the blood fraction, which typically contains approximately 5% of pre-β HDL particles, the concentration of pre-β HDL particles is substantially increased.

Figure 1B:
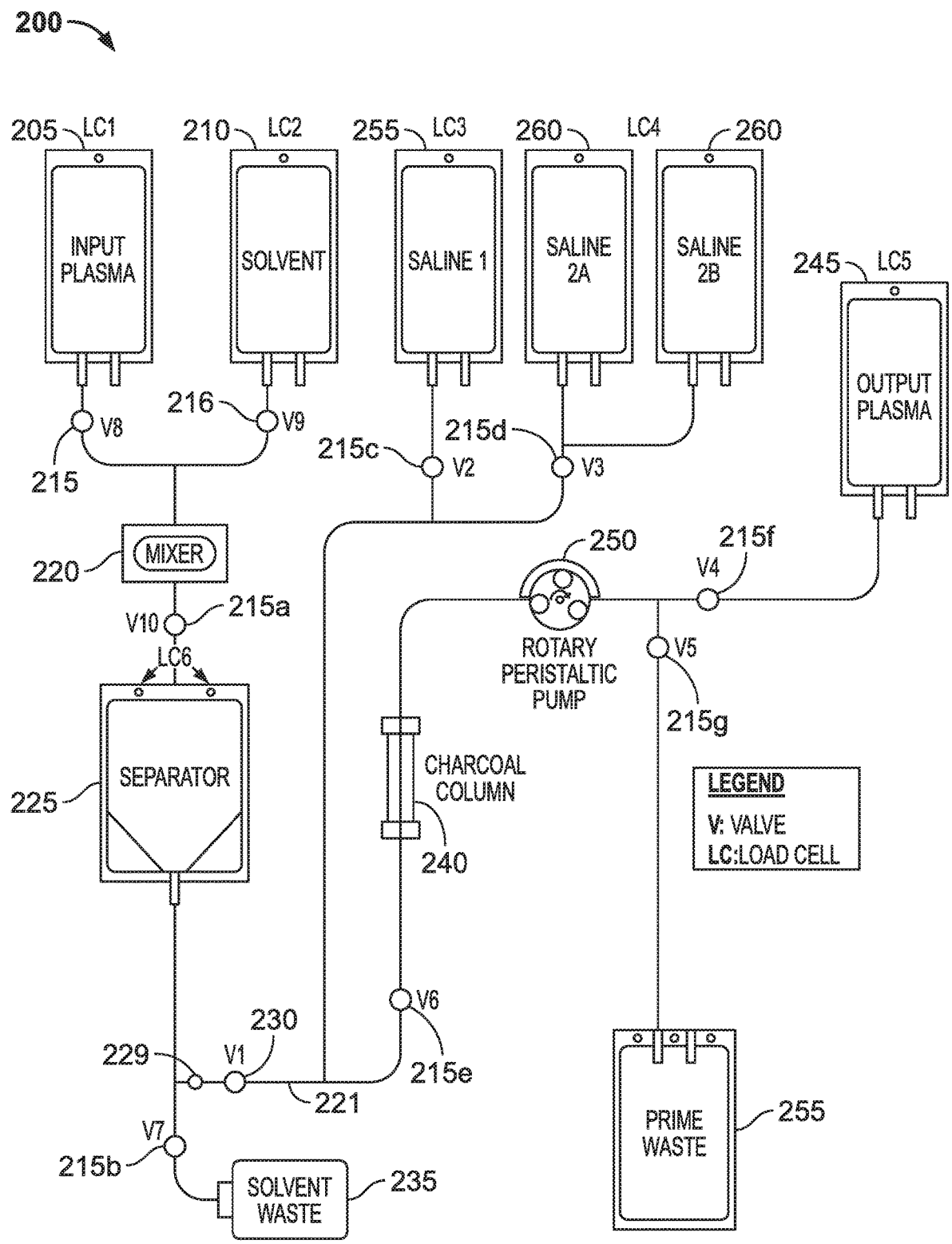
FIG. 1B is a schematic representation of a system comprising a plurality of components used in accordance with some embodiments of the present specification to achieve the processes disclosed herein.

FIG. 1B illustrates an exemplary embodiment of a system and its components used to achieve the methods of the present specification. The figure depicts an exemplary basic component flow diagram defining elements of the HDL modification system 200. Embodiments of the components of system 200 are utilized after obtaining a blood fraction from a patient or another individual (donor). The plasma, separated from the blood is brought in a sterile bag to system 200 for further processing. A fluid input 205 is provided and connected via tubing to a mixing device 220. A solvent input 210 is provided and also connected via tubing to mixing device 220. In embodiments, valves 215, 216 are used to control the flow of fluid from fluid input 205 and solvent from solvent input 210 respectively. It should be appreciated that the fluid input 205 contains any fluid that includes HDL particles, including plasma having LDL particles or devoid of LDL particles, as discussed above. It should further be appreciated that solvent input 210 can include a single solvent, a mixture of solvents, or a plurality of different solvents that are mixed at the point of solvent input 210. While depicted as a single solvent container, solvent input 210 can comprise a plurality of separate solvent containers. Embodiments of types of solvents that may be used are discussed above.

Mixer 220 mixes fluid from fluid input 205 and solvent from solvent input 210 to yield a fluid-solvent mixture. In embodiments, mixer 220 is capable of using a shaker bag mixing method with the input fluid and input solvent in a plurality of batches, such as 1, 2, 3 or more batches. An exemplary mixer is a Barnstead Labline orbital shaker table. Once formed, the fluid-solvent mixture is directed, through tubing and controlled by at least one valve 215a, to a separator 225. In an embodiment, separator 225 is capable of performing bulk solvent separation through gravity separation in a funnel-shaped bag.

In separator 225, the fluid-solvent mixture separates into a first layer and second layer. The first layer comprises a mixture of solvent and lipid that has been removed from the HDL particles. The first layer is transported through a valve 215b to a first waste container 235. The second layer comprises a mixture of residual solvent, modified HDL particles, and other elements of the input fluid. One of ordinary skill in the art would appreciate that the composition of the first layer and the second layer would differ based upon the nature of the input fluid. Once the first and second layers separate in separator 225, the second layer is transported through tubing to a solvent extraction device 240. In an embodiment, a pressure sensor 229 and valve 230 is positioned in the flow stream to control the flow of the second layer to solvent extraction device 240.

The opening and closing of valves 215, 216 to enable the flow of fluid from input containers 205, 210 may be timed using mass balance calculations derived from weight determinations of the fluid inputs 205, 210 and separator 225. For example, the valve 215b between separator 225 and first waste container 235 and valve 230 between separator 225 and solvent extraction device 240 open after the input masses (fluid and solvent) substantially balances with the mass in separator 225 and a sufficient period of time has elapsed to permit separation between the first and second layers. Depending on what solvent is used, and therefore which layer settles to the bottom of separator 225, either valve 215b between separator 225 and first waste container 235 is opened or valve 230 between separator 225 and solvent extraction device 240 is opened. One of ordinary skill in the art would appreciate that the timing of the opening is dependent upon how much fluid is in the first and second layers and would further appreciate that it is preferred to keep valve 215b between separator 225 and first waste container 235 open just long enough to remove all of the first layer and some of the second layer, thereby ensuring that as much solvent as possible has been removed from the fluid being sent to solvent extraction device 240.

In embodiments, a glucose input 255 and one or more saline inputs 260 are in fluid communication with the fluid path 221 leading from separator 225 to solvent extraction device 240. A plurality of valves 215c and 215d are also incorporated in the flow stream from glucose input 255 and saline input 260 respectively, to the tubing providing the flow path 221 from separator 225 to solvent extraction device 240. Glucose and saline are incorporated into embodiments of the present specification in order to prime solvent extraction device 240 prior to operation of the system. Where such priming is not required, the glucose and saline inputs are not required. Also, one of ordinary skill in the art would appreciate that the glucose and saline inputs can be replaced with other primers if solvent extraction device 240 requires it.

In some embodiments, solvent extraction device 240 is a charcoal column designed to remove the specific solvent used in solvent input 210. An exemplary solvent extraction device 240 is an Asahi Hemosorber charcoal column. A pump 250 is used to move the second layer from separator 225, through solvent extraction device 240, and to an output container 245. In embodiments, pump 250 is a rotary peristaltic pump, such as a Masterflex Model 77201-62.

The first layer is directed to waste container 235 that is in fluid communication with separator 225 through tubing and at least one valve 215b. Additionally, other waste, if generated, can be directed from the fluid path connecting solvent extraction device 240 and output container 245 to a second waste container 255. Optionally, in an embodiment, a valve 215f is included in the path from the solvent extraction device 240 to the output container 245. Optionally, in an embodiment, a valve 215g is included in the path from the solvent extraction device 240 to the second waste container 255.

In an embodiment of the present specification, gravity is used, wherever practical, to move fluid through each of the plurality of components. For example, gravity is used to drain input plasma 205 and input solvent 210 into mixer 220. Where mixer 220 comprises a shaker bag and separator 225 comprises a funnel bag, fluid is moved from the shaker bag to the funnel bag and, subsequently, to first waste container 235, if appropriate, using gravity.

In an additional embodiment, not shown in FIG. 1B, the output fluid in output container 245 is subjected to a solvent detection system, or lipid removing agent detection system, to determine if any solvent, or other undesirable component, is in the output fluid. In one embodiment, the output fluid is subjected to sensors that are capable of determining the concentrations of solvents introduced in the solvent input, such as n-butanol or di-isopropyl ether. In embodiments, the sensors are capable of providing such concentration information on a real-time basis and without having to physically transport a sample of the output fluid, or air in the headspace, to a remote device.

In an embodiment, the output fluid is further processed, in a second stage, to separate or to isolate at least pre-β HDL particles, and if required then both α and pre-β HDL particles. In an embodiment, the second stage (as described below) occurs in a separate and discrete area from the delipidation process where the end product output fluid is transported to a processing lab or room. In an alternate embodiment, the second stage processing occurs in-line with the delipidation system, whereby the system is connected to an affinity column sub-system or ultracentrifugation sub-system. The resultant separated α and/or pre-β HDL particles are then introduced to the bloodstream of the patient.

In one embodiment, molecularly imprinted polymer technology is used to enable surface acoustic wave sensors. A surface acoustic wave sensor receives an input, through some interaction of its surface with the surrounding environment, and yields an electrical response, generated by the piezoelectric properties of the sensor substrate. To enable the interaction, molecularly imprinted polymer technology is used. Molecularly imprinted polymers are plastics programmed to recognize target molecules, like pharmaceuticals, toxins or environmental pollutants, in complex biological samples. The molecular imprinting technology is enabled by the polymerization of one or more functional monomers with an excess of a crosslinking monomer in presence of a target template molecule exhibiting a structure similar to the target molecule that is to be recognized, i.e. the target solvent.

The use of molecularly imprinted polymer technology to enable surface acoustic wave sensors can be made more specific to the concentrations of targeted solvents and are capable of differentiating such targeted solvents from other possible interferents. As a result, the presence of acceptable interferents that may have similar structures and/or properties to the targeted solvents would not prevent the sensor from accurately reporting existing respective solvent concentrations.

Alternatively, if the input solvent comprises certain solvents, such as n-butanol, electrochemical oxidation could be used to measure the solvent concentration. Electrochemical measurements have several advantages. They are simple, sensitive, fast, and have a wide dynamic range. The instrumentation is simple and not affected by humidity. In one embodiment, the target solvent, such as n-butanol, is oxidized on a platinum electrode using cyclic voltammetry. This technique is based on varying the applied potential at a working electrode in both the forward and reverse directions, at a predefined scan rate, while monitoring the current. One full cycle, a partial cycle, or a series of cycles can be performed. While platinum is the preferred electrode material, other electrodes, such as gold, silver, iridium, or graphite, could be used. Although, cyclic voltammetric techniques are used, other pulse techniques such as differential pulse voltammetry or square wave voltammetry may increase the speed and sensitivity of measurements.

Embodiments of the present specification expressly cover any and all forms of automatically sampling and measuring, detecting, and analyzing an output fluid, or the headspace above the output fluid. For example, such automated detection can be achieved by integrating a mini-gas chromatography (GC) measuring device that automatically samples air in the output container, transmits it to a GC device optimized for the specific solvents used in the delipidation process, and, using known GC techniques, analyzes the sample for the presence of the solvents.

Referring back to FIG. 1B, suitable materials for use in any of the apparatus components as described herein include materials that are biocompatible, approved for medical applications that involve contact with internal body fluids, and in compliance with U.S. PVI or ISO 10993 standards. Further, the materials do not substantially degrade from, for instance, exposure to the solvents used in the present invention, during at least a single use. The materials are sterilizable either by radiation or ethylene oxide (EtO) sterilization. Such suitable materials are capable of being formed into objects using conventional processes, such as, but not limited to, extrusion, injection molding and others. Materials meeting these requirements include, but are not limited to, nylon, polypropylene, polycarbonate, acrylic, polysulfone, polyvinylidene fluoride (PVDF), fluoroelastomers such as VITON, available from DuPont Dow Elastomers L.L.C., thermoplastic elastomers such as SANTOPRENE, available from Monsanto, polyurethane, polyvinyl chloride (PVC), polytetrafluoroethylene (PTFE), polyphenylene ether (PFE), perfluoroalkoxy copolymer (PFA), which is available as TEFLON PFA from E.I. du Pont de Nemours and Company, and combinations thereof.

Valves 215, 215a, 215b, 215c, 215d, 215e, 215f, 215g, 216 and any other valve used in each embodiment may be composed of, but are not limited to, pinch, globe, ball, gate or other conventional valves. In some embodiments, the valves are occlusion valves such as Acro Associates' Model 955 valve. However, the present specification is not limited to a valve having a particular style. Further, the components of each system described in accordance with embodiments of the present specification may be physically coupled together or coupled together using conduits that may be composed of flexible or rigid pipe, tubing or other such devices known to those of ordinary skill in the art.

Figure 1C:
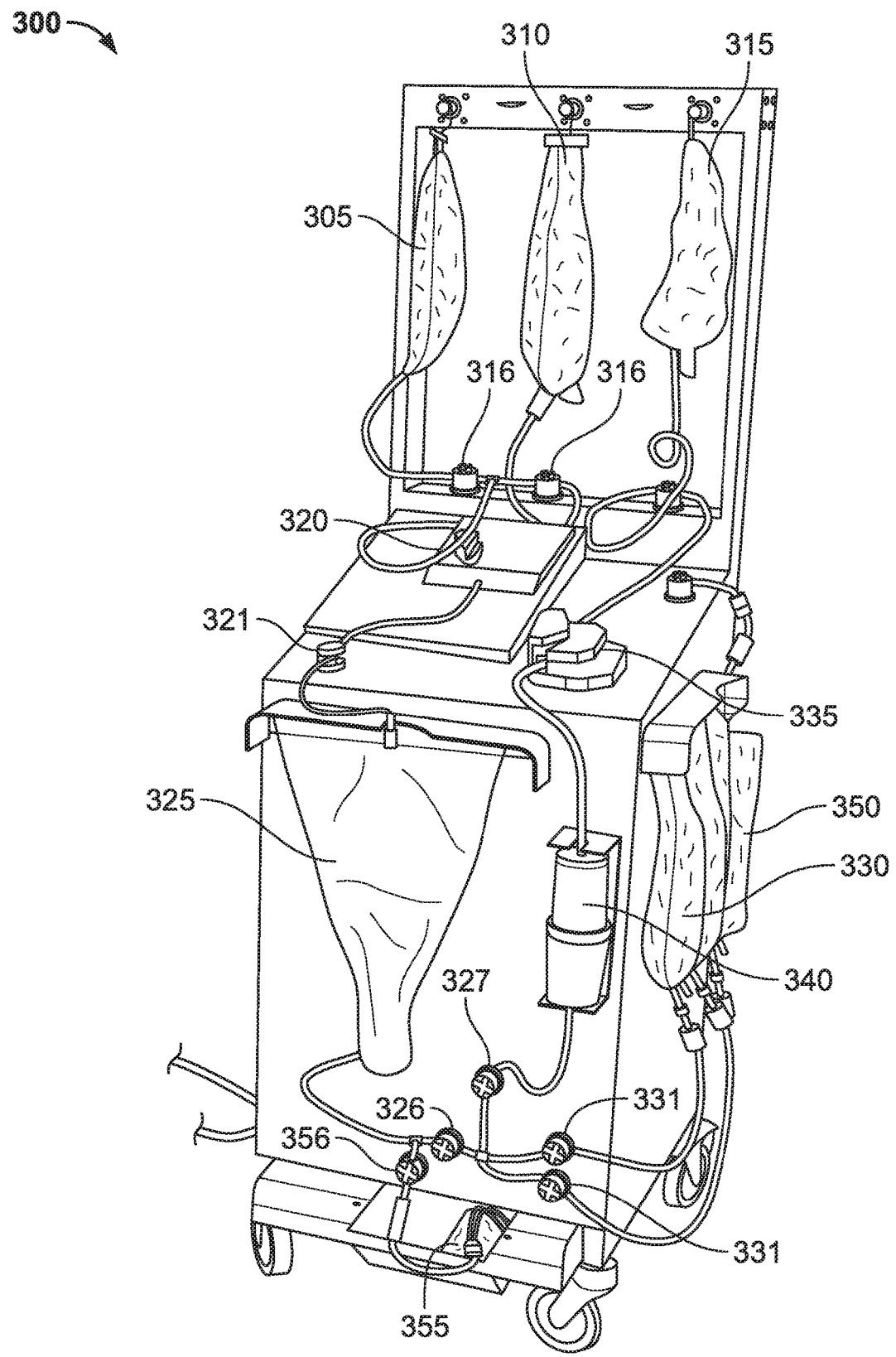
FIG. 1C is a pictorial illustration of an exemplary embodiment of a system configuration of a plurality of components used in accordance with some embodiments of the present specification to achieve the processes disclosed herein.

FIG. 1C illustrates an exemplary configuration of a system used in accordance with some embodiments of the present specification to achieve the processes disclosed herein. Referring to FIG. 1C, a configuration of basic components of the HDL modification system 300 is shown. A fluid input 305 is provided and connected via tubing to a mixing device 320. A solvent input 310 is provided and also connected via tubing to a mixing device 320. Preferably valves 316 are used to control the flow of fluid from fluid input 305 and solvent from solvent input 310. It should be appreciated that the fluid input 305 preferably contains any fluid that includes HDL particles, including plasma having LDL particles or devoid of LDL particles, as discussed above. It should further be appreciated that solvent input 310 can include a single solvent, a mixture of solvents, or a plurality of different solvents that are mixed at the point of solvent input 310. While depicted as a single solvent container, solvent input 310 can comprise a plurality of separate solvent containers. The types of solvents that are used and preferred are discussed above.

The mixer 320 mixes fluid from fluid input 305 and solvent from solvent input 310 to yield a fluid-solvent mixture. Preferably, mixer 320 is capable of using a shaker bag mixing method with the input fluid and input solvent in a plurality of batches, such as 1, 2, 3 or more batches. Once formed, the fluid-solvent mixture is directed, through tubing and controlled by at least one valve 321, to a separator 325. In a preferred embodiment, separator 325 is capable of performing bulk solvent separation through gravity separation in a funnel-shaped bag.

In the separator 325, the fluid-solvent mixture separates into a first layer and second layer. The first layer comprises a mixture of solvent and lipid that has been removed from the HDL particles. The second layer comprises a mixture of residual solvent, modified HDL particles, and other elements of the input fluid. One of ordinary skill in the art would appreciate that the composition of the first layer and the second layer would differ based upon the nature of the input fluid. Once the first and second layers separate in separator 325, the second layer is transported through tubing to a solvent extraction device 340. Preferably, a pressure sensor 326 and valve 327 is positioned in the flow stream to control the flow of the second layer to the solvent extraction device 340.

Preferably, a glucose input 330 and saline input 350 is in fluid communication with the fluid path leading from the separator 325 to the solvent extraction device 340. A plurality of valves 331 is also preferably incorporated in the flow stream from the glucose input 330 and saline input 350 to the tubing providing the flow path from the separator 325 to the solvent extraction device 340. Glucose and saline are incorporated into the present invention in order to prime the solvent extraction device 340 prior to operation of the system. Where such priming is not required, the glucose and saline inputs are not required. Also, one of ordinary skill in the art would appreciate that the glucose and saline inputs can be replaced with other primers if the solvent extraction device 340 requires it.

The solvent extraction device 340 is preferably a charcoal column designed to remove the specific solvent used in the solvent input 310. An exemplary solvent extraction device 340 is an Asahi Hemosorber charcoal column. A pump 335 is used to move the second layer from the separator 325, through the solvent extraction device 340, and to an output container 315. The pump is preferably a peristaltic pump, such as a Masterflex Model 77201-62.

The first layer is directed to a waste container 355 that is in fluid communication with separator 325 through tubing and at least one valve 356. Additionally, other waste, if generated, can be directed from the fluid path connecting solvent extraction device 340 and output container 315 to waste container 355.

Preferably, an embodiment of the present invention uses gravity, wherever practical, to move fluid through each of the plurality of components. For example, preferably gravity is used to drain the input plasma 305 and input solvent 310 into the mixer 320. Where the mixer 320 comprises a shaker bag and separator 325 comprises a funnel bag, fluid is moved from the shaker bag to the funnel bag and, subsequently, to the waste container 355, if appropriate, using gravity.

In general, the present invention preferably comprises configurations wherein all inputs, such as input plasma and input solvents, disposable elements, such as mixing bags, separator bags, waste bags, solvent extraction devices, and solvent detection devices, and output containers are in easily accessible positions and can be readily removed and replaced by a technician.

To enable the operation of the above described embodiments of the present invention, it is preferable to supply a user of such embodiments with a packaged set of components, in kit form, comprising each component required to practice embodiments of the present specification. The kit may include an input fluid container (i.e. a high density lipoprotein source container), a lipid removing agent source container (i.e. a solvent container), disposable components of a mixer, such as a bag or other container, disposable components of a separator, such as a bag or other container, disposable components of a solvent extraction device (i.e. a charcoal column), an output container, disposable components of a waste container, such as a bag or other container, solvent detection devices, and, a plurality of valves for controlling the flow of input fluid (high density lipoprotein) from the input container and lipid removing agent (solvent) from the solvent container to the mixer, for controlling the flow of the mixture of lipid removing agent, lipid, and particle derivative to the separator, for controlling the flow of lipid and lipid removing agent to a waste container, for controlling the flow of residual lipid removing agent, residual lipid, and particle derivative to the extraction device, and for controlling the flow of particle derivative to the output container.

In one embodiment, a kit comprises a plastic container having disposable components of a mixer, such as a bag or other container, disposable components of a separator, such as a bag or other container, disposable components of a waste container, such as a bag or other container, and, a plurality of tubing and a plurality of valves for controlling the flow of input fluid (high density lipoprotein) from the input container and lipid removing agent (solvent) from the solvent container to the mixer, for controlling the flow of the mixture of lipid removing agent, lipid, and particle derivative to the separator, for controlling the flow of lipid and lipid removing agent to a waste container, for controlling the flow of residual lipid removing agent, residual lipid, and particle derivative to the extraction device, and for controlling the flow of particle derivative to the output container. Disposable components of a solvent extraction device (i.e. a charcoal column), the input fluid, the input solvent, and solvent extraction devices may be provided separately.

Extracting modified HDL by delipidating plasma may be referred to as a first stage of the methods described in embodiments of the present specification. In accordance with embodiments of the present specification, at 110, the delipidated plasma is preserved for subsequent, later use. In an embodiment, the delipidated plasma may be used after a prolonged time period, such as at least one year and more preferably at least two years. In an embodiment, the delipidated plasma may be stored for a predetermined time period, wherein the time period may be dependent on the preservation process employed.

The delipidated plasma (DP), in any aliquot or volume, may be preserved by utilizing suitable preservation methods, such as but not limited to freezing. In various embodiments, any means of preservation may be employed as long as the method retains a predefined amount of efficacy of the final product when compared to the freshly delipidated plasma. Accordingly, it is essential that the delipidated plasma, comprising pre-beta HDL, be evaluated using 2D gel spot testing or quality testing to certify that the pre-beta HDL has not degraded to free Apo A1. More specifically, the present invention subjects a predefined portion of the stored delipidated plasma, comprising pre-beta HDL, to 2D gel testing and certifies that the batch associated with the tested delipidated plasma is acceptable for administration to a patient if no more than 80% of the pre-beta HDL has degraded to Apo A1.

Figure 2:
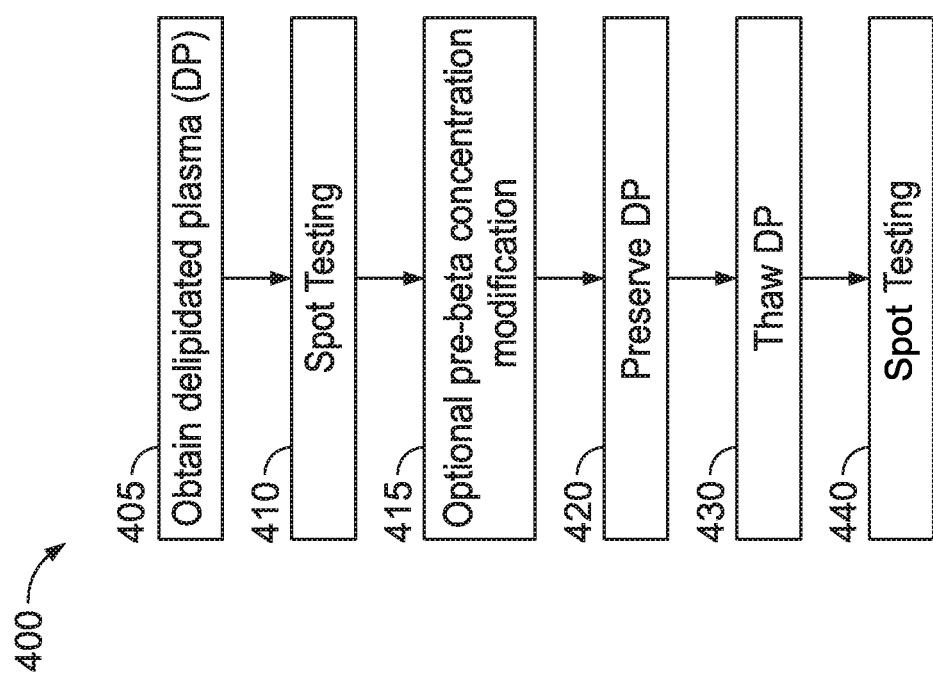
FIG. 2 is a flow chart illustrating a process for testing, preserving, and validating stored delipidated plasma comprising pre-beta HDL.

Referring to FIG. 2, a process 400 for acquiring, preserving, and thawing extracted delipidated plasma is shown. Extracted delipidated plasma, comprising pre-beta HDL, is obtained 405 using the processes described herein. Portions of a given batch of extracted delipidated plasma are spot tested 410 to establish baseline amounts or concentrations of pre-beta HDL. The spot testing 410 may be done using 2D gel electrophoresis in which a sample of the batch of extracted delipidated plasma is solubilized, loaded onto a gel, and subjected to an electric field which causes a movement of proteins, in accordance with their isoelectric points, through the gel. The separated proteins are then solubilized again and separated by their molecular weights on an orthogonal second axis. The spot testing 410 therefore quantifies a concentration or amount of proteins, such as pre-beta HDL, in the sample along two axes: isoelectric point and molecular weight. Other clinical evaluations are further described below.

Once spot tested 410, batches are subjected to preservation 420, preferably through flash freezing as further described below. In one embodiment, prior to preservation 420, the batch is optionally modified 415 to insure that the protein concentration of pre-beta HDL is within a predefined range, as further described below. It has been determined that preserved pre-beta HDL is less stable if the concentration of the preparation is too dilute and has decreased efficacy if the concentration of the preparation is too high. Accordingly, the batch is optionally modified, by dilution or concentration, 415 to insure that the concentration of pre-beta HDL in the delipidated plasma is within a range of 0.5 mg/dl to 500 mg/dl and preferably in a range of 1 mg/dl to 400 mg/dl, or any increment therein. Preferably, the concentration of pre-beta HDL in the delipidated plasma is no greater than 500 mg/dl.

After preservation 420, the delipidated plasma is stored, which can be for a week up to 3 years or any increment therein. At some point, the delipidated plasma is thawed 430. In one embodiment, thawing is achieved by taking the frozen delipidated plasma and placing it an environment having a temperature range of 2° C. to 26° C. In one embodiment, the thawing delipidated plasma is kept in an environment having a temperature range of 3° C. to 5° C. and more preferably 4° C. for a period of no more than 48 hours. Preferably, the thawed delipidated plasma is used within a 48 hour period of thawing, and more preferably within a 24 hour period, and is not re-frozen again. After thawing 430, a portion of the batch may be tested again 440 to determine if the pre-beta HDL in the delipidated plasma has degraded or is no longer effective, as further described below.

Optionally an additive may be included as part of the preservation process. An additive may be added to either the precursor or final product in order to enhance the preservation process. In embodiments, the DP is preserved using methods and standards similar to those applicable for preserving plasma. In an embodiment, the preservation is achieved by freezing. Some of these standard methods and practices are defined in the CFR and the AABB, ABC, ARC circular of Information for the Use of Human Blood and Blood Components, and by European Pharmacopeia guidelines for preparation of plasma for manufacturing. A volume or aliquot of the delipidated source plasma is placed in a freezer within a few hours of completing the delipidation process. In some embodiments, the DP is placed in a freezer within 8 hours of the delipidation process, or within a timeframe specified in the directions for use for the blood collecting, processing, and storage system. In embodiments, the DP volume is frozen per standard means for fresh frozen plasma at a temperature of approximately −18° C. to −80° C.

It should be noted herein that the volumes or aliquots indicated above are only exemplary and that any amount (volume or aliquot) of a delipidated plasma sample may be preserved using the systems and methods of the present specification. It should also be noted that multiple volumes or aliquots may be preserved either in series, where each volume or aliquot is sequentially preserved, or in parallel where multiple volumes or aliquots are preserved simultaneously.

Referring back to the preservation step, in one embodiment, and by way of example, 50 ml of delipidated plasma (DP) is frozen via flash freezing method using liquid nitrogen followed by storage at −80° C. In another embodiment, and by way of example, 50 ml of delipidated plasma (DP) is frozen using a slower freezing method at −80° C. In yet another embodiment, and by way of example, 50 ml of delipidated plasma (DP) is frozen using a slower freezing method at −20° C. in a frost-free freezer. In one embodiment, and by way of example, 100 ml of DP is frozen using a flash freezing method. In another embodiment, and by way of example, up to 400 ml of DP is frozen using a flash freezing methods. In other embodiments, DP volumes (units) ranging from at least 1 ml to 400 ml or higher volumes are frozen together using the preservation methods described above; any method of freezing may be used to preserve any volume of DP. The time needed to freeze a sample is size dependent; therefore, the amount of freezing time is different for different aliquot sizes. In embodiments, the time taken to freeze an aliquot size is also a function of the method used for freezing. In embodiments, the time needed to freeze a sample is predetermined and based on sample size and/or freezing method. In one embodiment, the time needed to flash freeze concentrated pre-beta HDL to −80° C. is less than 30 minutes, less than 20 minutes, and preferably less than 10 minutes. In another embodiment, the temperature for flash freezing is less than −30° C.

Other methods of freezing may be used in various embodiments of the present specification. The selected method of freezing would ensure that critical components of the DP are maintained. The duration of expiration of frozen delipidated plasma may vary for different freezing temperatures. Generally, for colder freezing temperatures, the product may be stored for a longer duration and thus, has a longer "shelf life" (slower expiration).

In embodiments, each unit of source plasma is assessed individually before and after the delipidation process. The plasma is assessed for parameters, including but not limited to the following parameters:
1. Concentration and size of pre-β and α HDL particles. In some embodiments, 2D gel electrophoresis technique is used with both heavy and light gels and immunoblotting for ApoA-I.
2. Clinical chemistry of the plasma. Various characteristics determined may include total cholesterol, HDL, LDL, ApoA-I, ApoB, triglycerides, CBC, sodium, potassium, chloride, calcium, phosphorous, creatinine, BUN, fibrinogen, aPTT, PT, ALT, AST, ALP, bilirubin, uric acid, glucose, LDH
3. Additionally, fractions of the DP, before freezing and after freezing and thawing in a subsequent step, is assessed for cholesterol content by UV absorbance using known techniques such as Fast Protein Liquid Chromatography (FPLC)).
4. Selective samples/fractions will be assayed for cholesterol efflux capacity, which include, but are not limited to the fractions delineated in FIGS. 1A and 1G.

In embodiments, the parameters described above are also assessed before preserving or freezing of the delipidated plasma and after thawing of the delipidated plasma. In some embodiments, the efficacy of the thawed delipidated plasma is in the range of 1% to 100% of the efficacy of the pre-preservation delipidated plasma. In some embodiments, the efficacy of the thawed delipidated plasma is in the range of 1% to 150% of the efficacy of the pre-preservation delipidated plasma. In some embodiments, the efficacy of the thawed delipidated plasma is in the range of 1% to 200% of the efficacy of the pre-preservation delipidated plasma. In some embodiments, the efficacy of the thawed delipidated plasma is lower than the efficacy of the pre-preservation delipidated plasma. In some embodiments, the efficacy of the thawed delipidated plasma is greater than the efficacy of the pre-preservation delipidated plasma.

At 112, the preserved DP, is prepared for normal use for further processing or for treating a patient. The patient treated by the DP may or may not be the individual from who the plasma was obtained for the delipidation process (it may be autologous or non-autologous). If, at 110, the DP was preserved by freezing, then at 112 it is prepared by thawing. In an embodiment, the frozen DP is thawed with a water bath at a temperature in the range of 30° C. to 37° C. for approximately 30 minutes. In some embodiments, the thawed plasma is maintained at 1° C. to 6° C. for 1-5 days. In one more embodiment, the frozen DP is thawed slowly at room temperature. In another embodiment, the frozen DP is thawed rapidly in a refrigerator at approximately 5° C. Other methods of thawing frozen DP may be utilized for different quantities and compositions of DP.

In various embodiments of the present specification, in a second stage, delipidated or modified HDL is further treated to separate or isolate components of HDL particles such as pre-β HDL particles or a combination of α and pre-β HDL particles. At 114, the treated and thawed plasma containing modified HDL particles with reduced lipid content, which was separated from the solvents at 108, is further treated with solvents to yield a solution comprising a higher concentration of α and pre-β HDL particles. Exemplary methods for separating alpha and pre-beta particles from delipidated plasma are discussed below.

At 116, in accordance with some optional embodiments of the present specification, the separated α and pre-β HDL particles are preserved by freezing and may be used after a prolonged period after thawing at 118. In one embodiment, thawing is achieved by taking the frozen delipidated plasma and placing it an environment having a temperature range of 2° C. to 26° C. In one embodiment, the thawing delipidated plasma is kept in an environment having a temperature range of 3° C. to 5° C. and more preferably 4° C. for a period of no more than 48 hours. Preferably, the thawed delipidated plasma is used within a 48 hour period of thawing, and more preferably within a 24 hour period, and is not re-frozen again. In embodiments, the process of preserving and preparing derived α and pre-β HDL particles is similar to the methods for preserving and preparing DP. In an embodiment, flash freezing methods are preferably used to freeze derived α and pre-β HDL particles.

Methods of Separating Pre-Beta Particles from Delipidated Plasma

In an embodiment, affinity chromatography may be used to reduce the amount of unwanted substances in delipidated plasma (for example, plasma proteins and certain lipoproteins, such as LDL and VLDL), and therefore increase the concentration of a desired substance (for example, pre-β HDL particles).

Figure 1F:
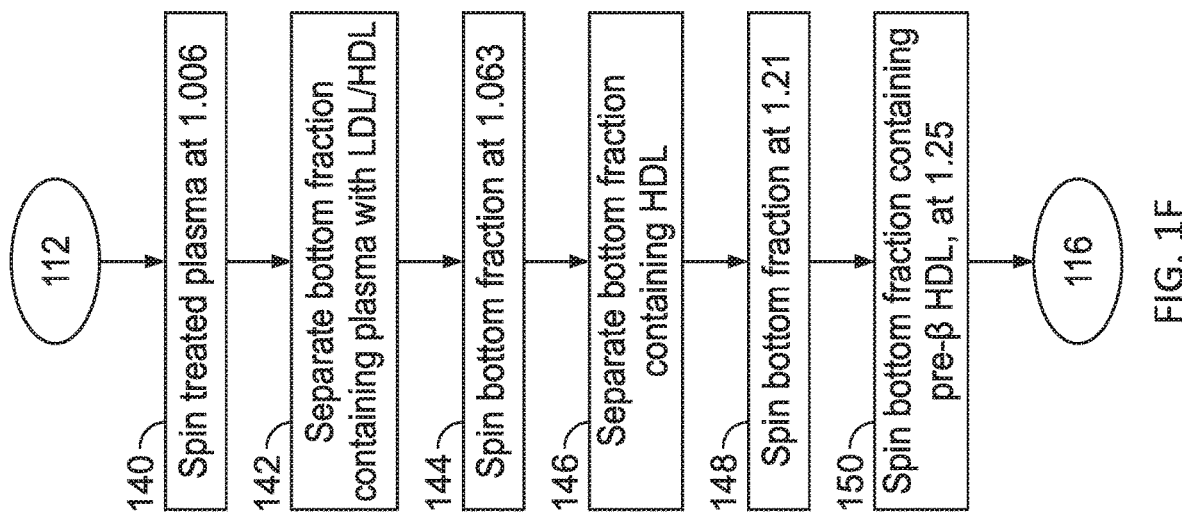
FIG. 1F is a flow chart illustrating another exemplary process used for increasing the concentration of desired substances in delipidated plasma, using ultracentrifugation, in accordance with some embodiments of the present specification.
Figure 1E:
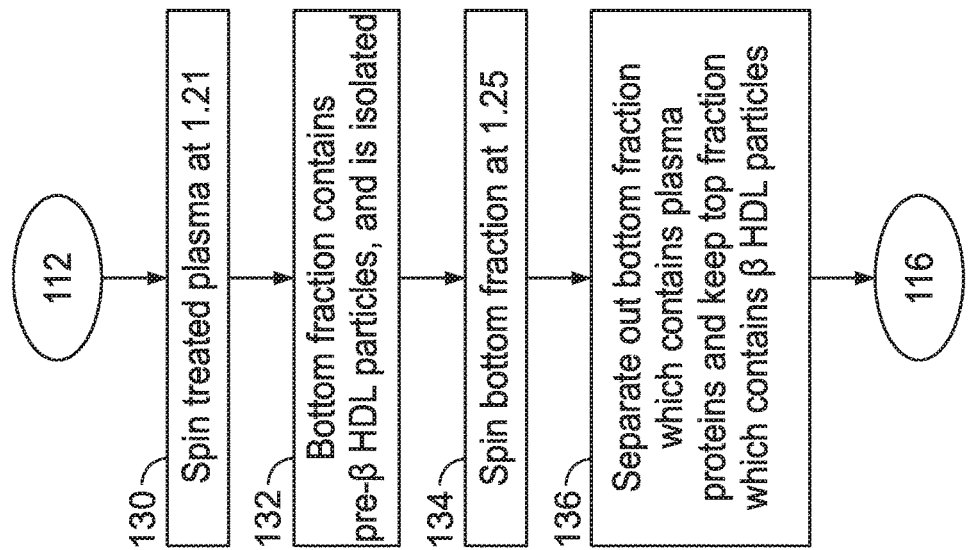
FIG. 1E is a flow chart illustrating an exemplary process used for increasing the concentration of desired substances in delipidated plasma, using ultracentrifugation, in accordance with some embodiments of the present specification.
Figure 1D:
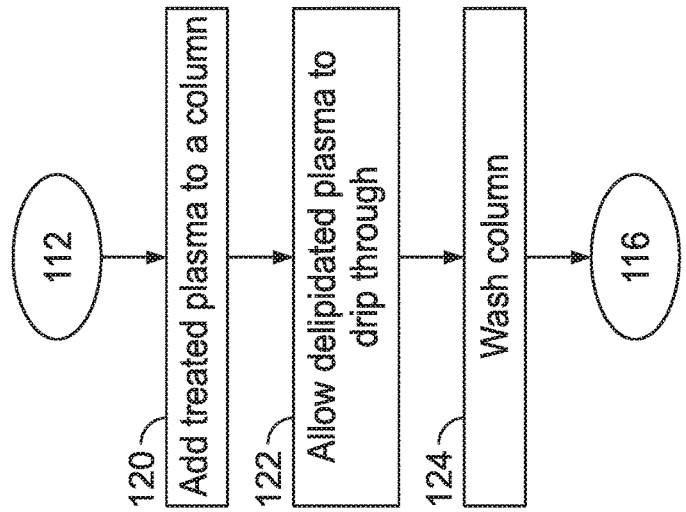
FIG. 1D is a flow chart illustrating an exemplary process used for increasing the concentration of desired substances in delipidated plasma using affinity chromatography, in accordance with some embodiments of the present specification.

FIG. 1D is a flow chart illustrating an exemplary set of steps that are used to increase the concentration of desired substances in the treated plasma, using affinity chromatography, in accordance with some embodiments of the present specification. In an embodiment, an affinity column is used to entrap ApoA-I protein particles (and therefore pre-β HDL) particles while removing undesired particles from the treated plasma. At 120, treated plasma is added to the column for affinity chromatography utilizing an antibody to ApoA-I so that ApoA-I is bound to the antibody when the treated plasma is run through the column. A solid medium, such as a resin, may be used to bind the desired substance in the form of HDL particles. The desired HDL particles may comprise a mixture of α-HDL and pre-β HDL particles. The composition of these particles is on the order of approximately 15% α-HDL and 85% pre-β particles. At 122, the unbound and unwanted substances, including LDL, and VLDL drip through the column (as they do not bind to the antibody to ApoA-I), and are thereby removed from the treated plasma solution. At 124, a washing buffer may be run through the column to remove any unwanted proteins. A disassociating reagent or solution is then run through the column so that the pre-β HDL particles (or ApoA-I) which contains the pre-β HDL particles) are no longer bound to the antibody to ApoA-I and are effectively separated.

Ultracentrifugation is another method that may be employed to reduce the amount of unwanted substances (for example, plasma proteins and certain lipoproteins, such as LDL and VLDL, and in this case, α HDL particles), and therefore increase the concentration of desired substance (for example, pre-β HDL particles). In this method, the principle of centrifugation is utilized to separate constituents of a solution by rotating the solution at very high speeds.

The starting material delipidated plasma solution has a density of 1006 kg/m3, or 1.006 g/ml. In order to separate out the various fractions during ultracentrifugation, as discussed below, it may be necessary to adjust the density of the starting material at each step. In embodiments, the density can be adjusted by adding a volume of a more dense substance or solvent (such as Potassium Bromide (KBr) to the treated plasma. In an embodiment, any solution having a density that can be used to adjust the density of the starting material may be employed.

In an embodiment, a concentrated stock solution of Potassium Bromide (KBr) and Sodium Chloride (NaCl), having a combined density of 1.346 is added to the delipidated/treated plasma solution to adjust the density of the treated plasma solution to a desired density. The stock solution has a density higher than 1.25 g/mL (for example, an aqueous solution of 4.62M KBr, has a density of 1.37 g/mL), while the treated plasma solution has a density of approximately 1.006 g/mL. The solution resulting from the addition of a dense substance to treated plasma will have a specific density that will allow for separation of the various fractions during ultracentrifugation. Methods for adjusting density are well known to those of ordinary skill in the art and also described in Havel et al., J. Clin. Invest. 1955, 34; 1345-1353, which discusses a method for separating and purifying lipoprotein fractions on a preparative scale for analysis and use in metabolic studies and which is herein incorporated by reference.

In an embodiment, the combined plasma and solvent are introduced into an ultracentrifugation tube (or may be combined in the tube itself). The tubes may be held by a rotor. The tubes may be spun at a high speed for sufficient time to produce a separation, following which the rotor comes to a smooth stop and a gradient is gently pumped out of each tube to isolate the separated components. In one embodiment, ultracentrifugation is performed at speeds of approximately 105,000×g and for roughly 16-20 hours. It should be noted that the spin time is adjusted based on the density of the starting material and the relative densities of the desired fractions that are to be separated out For example, if density of the material that is extracted in a first step is 1.21 g/mL and a subsequent density that is desired in a second step is 1.25 g/mL, it will take longer to separate out the two materials of similar density that it would take to separate out a density of 1.006 g/mL from a starting material having a density of 1.21 g/mL.

In embodiments, the resultant desired fraction includes at least pre-β HDL particles which are separated from the treated plasma.

FIG. 1E is a flow chart illustrating an exemplary set of steps that are used to increase the concentration of desired substances in the treated plasma, using ultracentrifugation, in accordance with some embodiments of the present specification. In an embodiment, the method described in this flow chart may be used to more quickly separate pre-β HDL using ultracentrifugation. At 130, a treated plasma starting material can be spun at an adjusted density of 1.21, which corresponds to the density of HDL. The top fraction will contain VLDL, LDL, and α HDL, while pre-β HDL will be in the bottom fraction. In an embodiment, the spinning is performed over a period of 18-24 hours. At 132, the bottom fraction containing pre-β HDL and plasma proteins is isolated. At 134, the isolated bottom fraction containing pre-β HDL is spun at a density of 1.25 yielding a top fraction containing pre-β HDL and a bottom fraction containing plasma proteins. In an embodiment, the spinning is performed over a period of 24-48 hours. At 136, the resultant top bottom fraction containing pre-β HDL is isolated from the bottom fraction containing plasma proteins, yielding a concentrated pre-β HDL product.

At the end of the process of ultracentrifugation, pre-β HDL particles float to the top, and may be separated to obtain a solution with a high concentration of pre-β HDL particles. Subsequently, the tube containing concentrated pre-β HDL particles may be detached.

FIG. 1F is a flow chart illustrating another exemplary set of steps that are used to increase the concentration of desired substances in the treated plasma, using ultracentrifugation, in accordance with some embodiments of the present specification.

In some embodiments, ultracentrifugation is a stepwise process that is performed at different densities. Since lipoproteins are lighter than proteins, it is possible to separate them from the delipidated (treated) plasma using ultracentrifugation at different densities to achieve sequential fractionation. At 140, the delipidated (treated) plasma is spun at a density of 1.006 for 18-24 hours, which corresponds to the density of plasma (1006 kg/m3, or 1.006 g/ml). At this stage, the proteins are at the bottom of the centrifugation tube, while VLDL resides at the top. In addition, plasma containing LDL and HDL is at the bottommost portion of the tube.

At step 142, the fraction containing the plasma with LDL/HDL is separated from the other constituents in the tube.

At step 144, the plasma containing LDL/HDL (plus a solution to adjust the density) is spun at a density of 1.063, which corresponds to the density of LDL. The result is a fraction containing LDL at the top and a fraction containing HDL at the bottom of the tube.

At step 146, the bottom fraction containing the HDL is separated from the other constituents in the tube.

At step 148, the HDL fraction is spun at a density of 1.21, which corresponds to the density of HDL. The end result is a fraction containing HDL at the top and pre-beta HDL at the bottom of the tube.

At step 150, the bottom fraction containing the pre-beta HDL is spun at a density of 1.25. The end result is a fraction containing pre-beta HDL at the top of the tube and the remaining plasma constituents at the bottom of the tube. At the end of the process of ultracentrifugation, pre-β HDL particles float to the top, and may be separated to obtain a solution with a high concentration of pre-β HDL particles. Subsequently, the tube containing concentrated pre-β HDL particles may be detached. The isolated lipoprotein fractions are separated from KBr using dialysis, gel filtration or other suitable methodologies.

It may be understood by persons skilled in the art that the fractions derived through spinning the treated plasma can be separated in different ways, and is not limited to the methods described in context of FIGS. 1E and 1F.

Figure 1G:
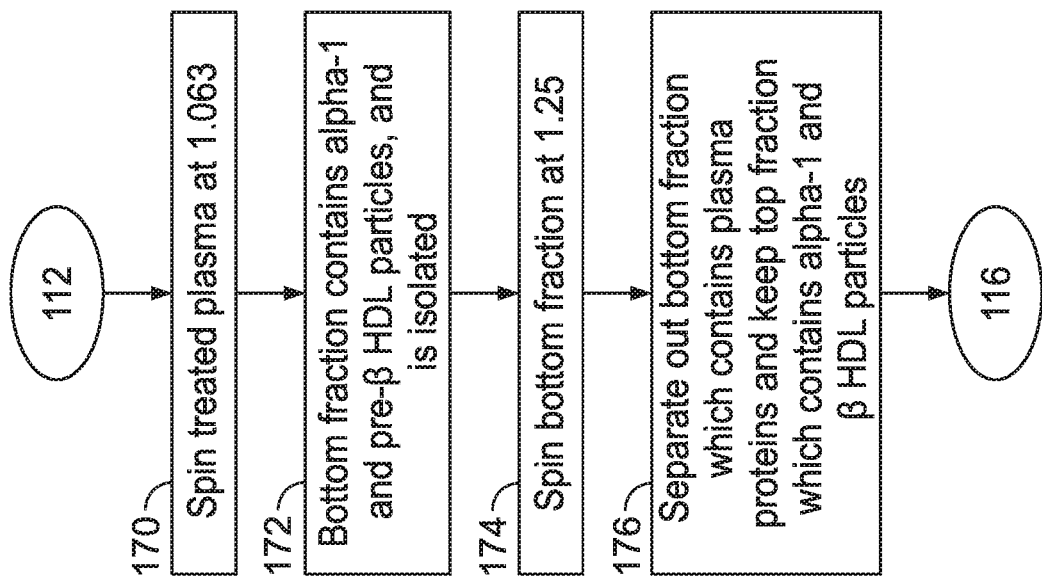
FIG. 1G is a flow chart illustrating another exemplary set of steps that are used to increase the concentration of desired substances in the treated plasma, using ultracentrifugation, in accordance with some embodiments of the present specification.

FIG. 1G is a flow chart illustrating another exemplary set of steps that are used to increase the concentration of desired substances in the treated plasma, using ultracentrifugation, in accordance with some embodiments of the present specification. In an embodiment, the method described in this flow chart may be used to more quickly separate both α (alpha-1) and pre-β HDL from delipidated plasma using ultracentrifugation. At 170, a treated plasma starting material can be spun at an adjusted density of 1.063, which corresponds to the density of LDL. The result is a fraction containing LDL at the top and a fraction containing HDL at the bottom of the tube. In an embodiment, the spinning is performed over a period of 18-24 hours. At 172, the bottom fraction containing alpha-1 and pre-β HDL and plasma proteins is isolated. At 174, the isolated bottom fraction containing alpha-1 and pre-β HDL is spun at a density of 1.25 yielding a top fraction containing alpha-1 and pre-β HDL and a bottom fraction containing plasma proteins. In an embodiment, the spinning is performed over a period of 24-48 hours. At 176, the resultant top fraction containing alpha-1 and pre-β HDL is isolated from the bottom fraction containing plasma proteins, yielding a concentrated product comprising alpha-1 and pre-β HDL.

At the end of the process of ultracentrifugation, alpha-1 and pre-β HDL particles float to the top, and may be separated to obtain a solution with a high concentration of alpha-1 and pre-β HDL particles. Subsequently, the tube containing concentrated alpha-1 and pre-β HDL particles may be detached. The isolated lipoprotein fractions are separated from KBr by dialysis, gel filtration or other suitable methodologies.

Referring back to FIG. 1A, at 160, the treated plasma containing concentrated solution of pre-β HDL or a combination of α and pre-β HDL particles with reduced lipid content is separated from the solvents, treated appropriately, and subsequently delivered to the patient. The delivered solution has a further increased concentration of α and/or pre-beta HDL. The resulting treated plasma containing the HDL particles with reduced lipid and increased pre-beta concentration is provided to the patient following dialysis with saline. In case of affinity chromatography, dialysis also releases entrapped desired substances (concentrated pre-β HDL particles). In case of autologous plasma, if the red cells of the patient were not already returned during plasmapheresis, they may be administered to the patient at some point during the procedure. In an optional embodiment, the red blood cells may be returned to the patient after combining them with the isolated α and/or pre-β HDL particles. One route of administration is through the vascular system, preferably intravenously.

In another alternative embodiment, a two stage process is applied to completely isolate pre-β HDL particles. First, affinity chromatography is used to separate a solution comprising both pre-β and α HDL particles. Following which, ultracentrifugation is used to fully isolate pre-β HDL particles.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method for preserving pre-beta high density lipoprotein for administration to a patient, comprising:
    obtaining a batch of delipidated plasma comprising the pre-beta high density lipoprotein;
    testing a portion of the batch of the delipidated plasma to characterize the pre-beta high density lipoprotein in order to, at least in part, determine a first characteristic of the pre-beta high density lipoprotein, wherein the first characteristic comprises a first concentration of the pre-beta high density lipoprotein in the delipidated plasma;
    preserving the batch of the delipidated plasma;
    after a period of time, preparing the preserved delipidated plasma for administration to the patient, wherein the period of time ranges from one week to three years;
    testing a portion of the prepared preserved delipidated plasma by acquiring a first amount of the pre-beta high density lipoprotein, determining a second characteristic of the pre-beta high density lipoprotein from the prepared preserved delipidated plasma, wherein the second characteristic comprises a second concentration of the pre-beta high density lipoprotein in the prepared preserved delipidated plasma, comparing the second characteristic of the pre-beta high density lipoprotein to the first characteristic of the pre-beta high density lipoprotein to determine an extent of degradation, and determining if the prepared preserved delipidated plasma is suitable for administration based on the second characteristic of the pre-beta high density lipoprotein; and
    administering the prepared preserved delipidated plasma to the patient.

2. The method of claim 1, further comprising, prior to said preserving, modifying an amount of the pre-beta high density lipoprotein to ensure a concentration of the pre-beta high density lipoprotein is in a range of 1 mg/dl to 400 mg/dl.

3. The method of claim 1, wherein said preserving comprises freezing the batch at a temperature less than −30° C.

4. The method of claim 1, wherein said preparing comprises thawing the preserved delipidated plasma in a temperature range of 2° C. to 26° C.

5. The method of claim 1, wherein said preserving comprises subjecting a volume of the delipidated plasma in a range from 1 milliliter to 2 liters to a temperature of less than −30° C. for less than 20 minutes.

6. The method of claim 1, further comprising, prior to said preservation, adding a preservative to the delipidated plasma.

7. The method of claim 1, wherein said preparing comprises thawing the preserved delipidated plasma and further comprising storing the thawed delipidated plasma at a temperature in a range of 1° C. to 6° C. for no more than 5 days.

8. A method for preserving modified high density lipoproteins for administration to a patient, comprising:
    obtaining a batch of delipidated plasma comprising the modified high density lipoproteins by connecting at least one person to a device for withdrawing blood, withdrawing blood containing blood cells from the at least one person, separating the blood cells from the blood to yield a blood plasma fraction containing high density lipoproteins and low density lipoproteins, delipidating the high density lipoproteins using a solvent, separating out the low density lipoproteins, and collecting the delipidated plasma with the modified high density lipoproteins;

testing a portion of the batch of the delipidated plasma to characterize the modified high density lipoproteins in order to, at least in part, determine a first characteristic of the modified high density lipoprotein, wherein the first characteristic comprises a first concentration of the modified density lipoprotein in the delipidated plasma;

preserving the batch of the delipidated plasma;

after a period of time, preparing the preserved delipidated plasma for administration to the patient, wherein the period of time ranges from one week to three years;

testing a portion of the prepared preserved delipidated plasma by acquiring a first amount of the modified high density lipoprotein, determining a second characteristic of the modified high density lipoprotein from the prepared preserved delipidated plasma, wherein the second characteristic comprises a second concentration of the pre-beta high density lipoprotein in the prepared preserved delipidated plasma, comparing the second characteristic of the modified high density lipoprotein to the first characteristic of the modified high density lipoprotein to determine an extent of degradation, and determining if the prepared preserved delipidated plasma is suitable for administration based on the second characteristic of the modified high density lipoprotein; and administering the prepared preserved delipidated plasma to the patient.

9. The method of claim 8, further comprising, prior to said preserving, modifying an amount of the modified high density lipoproteins to ensure a concentration of the modified high density lipoproteins is in a range of 1 mg/dl to 400 mg/dl.

10. The method of claim 8, wherein said preserving comprises freezing the batch at a temperature less than −30° C.

11. The method of claim 8, wherein said preparing comprises thawing the preserved delipidated plasma in a temperature range of 2° C. to 26° C.

12. The method of claim 8, wherein said preserving comprises subjecting a volume of the delipidated plasma in a range from 1 milliliter to 2 liters to a temperature less than −30° C. for less than 20 minutes.

13. The method of claim 8, further comprising, prior to said preservation, adding a preservative to the delipidated plasma.

14. The method of claim 8, wherein said preparing comprises thawing the preserved delipidated plasma and further comprising storing the thawed delipidated plasma at a temperature in a range of 1° C. to 6° C. for no more than 5 days.

* * * * *